United States Patent
Wu et al.

(10) Patent No.: US 10,781,265 B2
(45) Date of Patent: Sep. 22, 2020

(54) HUMANIZED ANTIBODIES AGAINST GLOBO H AND USES THEREOF IN CANCER TREATMENTS

(71) Applicant: Development Center for Biotechnology, New Taipei (TW)

(72) Inventors: Chia-Cheng Wu, New Taipei (TW);
Szu-Liang Lai, New Taipei (TW);
Yu-Jung Chen, New Taipei (TW);
Chih-Yung Hu, New Taipei (TW);
Tzu-Yin Lin, New Taipei (TW)

(73) Assignee: Development Center for Biotechnology, New Taipei (TW)

( * ) Notice: Subject to any disclaimer, the term of this patent is extended or adjusted under 35 U.S.C. 154(b) by 0 days.

(21) Appl. No.: 15/988,875

(22) Filed: May 24, 2018

(65) Prior Publication Data

US 2020/0048365 A1 Feb. 13, 2020

Related U.S. Application Data

(60) Provisional application No. 62/510,742, filed on May 24, 2017.

(51) Int. Cl.
*C07K 16/34* (2006.01)

(52) U.S. Cl.
CPC .................................. *C07K 16/34* (2013.01)

(58) Field of Classification Search
None
See application file for complete search history.

(56) References Cited

FOREIGN PATENT DOCUMENTS

WO 2015143123 * 9/2015

* cited by examiner

*Primary Examiner* — Karl J Puttlitz
(74) *Attorney, Agent, or Firm* — Liang Legal Group, PLLC

(57) ABSTRACT

A humanized anti-Globo H antibody, or an scFv or Fab fragment thereof, comprising a heavy-chain variable domain having three complementary regions consisting of HCDR1, HCDR2, and HCDR3 and a light-chain variable domain having three complementary regions consisting of LCDR1, LCDR2, and LCDR3, wherein the sequence of HCDR1 is GYISSDQILN (SEQ ID NO:4), the sequence of HCDR2 is RIYPVTGVTQYXHKFVG (SEQ ID NO:5, wherein X is any amino acid), and the sequence of HCDR3 is GETFDS (SEQ ID NO:6), wherein the sequence of LCDR1 is KSN-QNLLX'SGNRRYZLV (SEQ ID NO:7, wherein X' is F, Y, or W, and Z is C, G, S or T), the sequence of LCDR2 is WASDRSF (SEQ ID NO:8), and the sequence of LCDR3 is QQHLDIPYT (SEQ ID NO:9).

13 Claims, 21 Drawing Sheets

Specification includes a Sequence Listing.

FIG. 8 A

| | SEQ ID NO | |
|---|---|---|
| GBH (M) | 10 | QIQLHQSGIELASPGSSITLSCKPS[HCDR1]WVKKR |
| GBH (H) | 11 | EVQLVESGGGLVQPGGSLRLSCAAS[HCDR1]WVRQA |
| GBH (B1) | 12 | QIQLVESGGGLVQPGGSLRLSCAPS[HCDR1]WVKKA |
| GBH (Re2) | 13 | EIQLVQSGGGLAQPGGSIRLSCAPS[HCDR1]WVKKA |
| GBH (B11) | 14 | EIQLVQSGGGLAQPGGSIRLSCAPS[HCDR1]WVKKA |

| | | |
|---|---|---|
| GBH (M) | | PGQGLEWIG[HCDR2]KATFSVDRSSDTVRM |
| GBH (H) | | PGKGLEWVA[HCDR2]RFTISRDDSKNTLYL |
| GBH (B1) | | PGKGLEWIG[HCDR2]KATFSVDRSKDTVYL |
| GBH (Re2) | | PGKGLEWIG[HCDR2]KATFSVDRSKDTVYM |
| GBH (B11) | | PGKGLEWIG[HCDR2]KATFSVDRSKDTVYM |

| | | |
|---|---|---|
| GBH (M) | | VMNSLTSEDSGVYYCGR[HCDR3]WGQGTILTVSS |
| GBH (H) | | QMNSLRAEDTAVYYCAR[HCDR3]WGQGTLVTVSS |
| GBH (B1) | | QMNSLRAEDTAVYYCGR[HCDR3]WGQGTLVTVSS |
| GBH (Re2) | | QMNSLRAEDTGVYYCGR[HCDR3]WGQGTLLTVSS |
| GBH (B11) | | QMNSLRAEDTGVYYCGR[HCDR3]WGQGTLLTVSS |

FIG. 8 B

| | SEQ ID NO | |
|---|---|---|
| GBH (M) | 15 | EIVLTQSIPSLTVSAGERVTINC[LCDR1]WHQWK |
| GBH (H) | 16 | DIQMTQSPSSLSASVGDRVTITC[LCDR1]WYQQK |
| GBH (B1) | 17 | EIVLTQSPSSLSASVGDRVTINC[LCDR1]WHQWK |
| GBH (Re2) | 18 | DIQLTQSISSLSVSVGDRVTINC[LCDR1]WHQWK |
| GBH (B11) | 19 | DIQLTQSISSLSVSVGDRVTINC[LCDR1]WHQWK |

| | | |
|---|---|---|
| GBH (M) | | PGQSPKPLIT[LCDR2]GVPDRFIGGGSVTDFTLTISSVRA |
| GBH (H) | | PGKAPKLLIY[LCDR2]GVPSRFSGSGSGTDFTLTISSLQP |
| GBH (B1) | | PGKAPKPLIT[LCDR2]GVPSRFSGSGSVTDFTLTISSLQP |
| GBH (Re2) | | PGKSPKPLIT[LCDR2]GVPSRFSGSGSVTDFTLTISSVQP |
| GBH (B11) | | PGKSPKPLIT[LCDR2]GVPSRFSGSGSVTDFTLTISSVQP |

| | | |
|---|---|---|
| GBH (M) | | EDVAVYFC[LCDR3]FGGGTKLEIKR |
| GBH (H) | | EDFATYYC[LCDR3]FGQGTKVEIKR |
| GBH (B1) | | EDFATYFC[LCDR3]FGQGTKVEIKR |
| GBH (Re2) | | EDFAVYFC[LCDR3]FGGGTKLEIKR |
| GBH (B11) | | EDFAVYFC[LCDR3]FGGGTKLEIKR |

|          | SEQ ID NO |                                                                 |
|----------|-----------|-----------------------------------------------------------------|

HCDR1

GBH (C)    20   EIQLVQSGGGLAQPGGSIRLSCAPS[GYISSDQILN]WVKKA
GBH (B13)  21   EIQLVQSGGGLAQPGGSIRLSCAPS[GYISSDQILN]WVKKA

HCDR2

GBH (C)         PGKGLEWIG[RIYPVTGVT X YNHKFVG]KATFSVDRSKDTVYM
GBH (B13)       PGKGLEWIG[RIYPVTGVTQYNHKFVG]KATFSVDRSKDTVYM

HCDR3

GBH (C)         QMNSLRAEDTGVYYCGR[GETFDS]WGQGTLLTVSS
GBH (B13)       QMNSLRAEDTGVYYCGR[GETFDS]WGQGTLLTVSS

Wherein X is any amino acid.

FIG. 9 A

SEQ ID NO

LCDR1

GBH (C)    22   DIQLTQSISSLSVSVGDRVTINC[KSNQNLL X SGNRRY Z LV]WHQWK
GBH (B13)  23   DIQLTQSISSLSVSVGDRVTINC[KSNQNLLWSGNRRYTLV]WHQWK

LCDR2

GBH (C)         PGKSPKPLIT[WASDRSF]GVPSRFSGSGSVTDFTLTISSVQP
GBH (B13)       PGKSPKPLIT[WASDRSF]GVPSRFSGSGSVTDFTLTISSVQP

LCDR3

GBH (C)         EDFAVYFC[QQHLDIPYT]FGGGTKLEIKR
GBH (B13)       EDFAVYFC[QQHLDIPYT]FGGGTKLEIKR

Wherein X is F, W, or Y; and
        Z is C, G, T, or S.

FIG. 9 B

FIG. 11 A MCF7
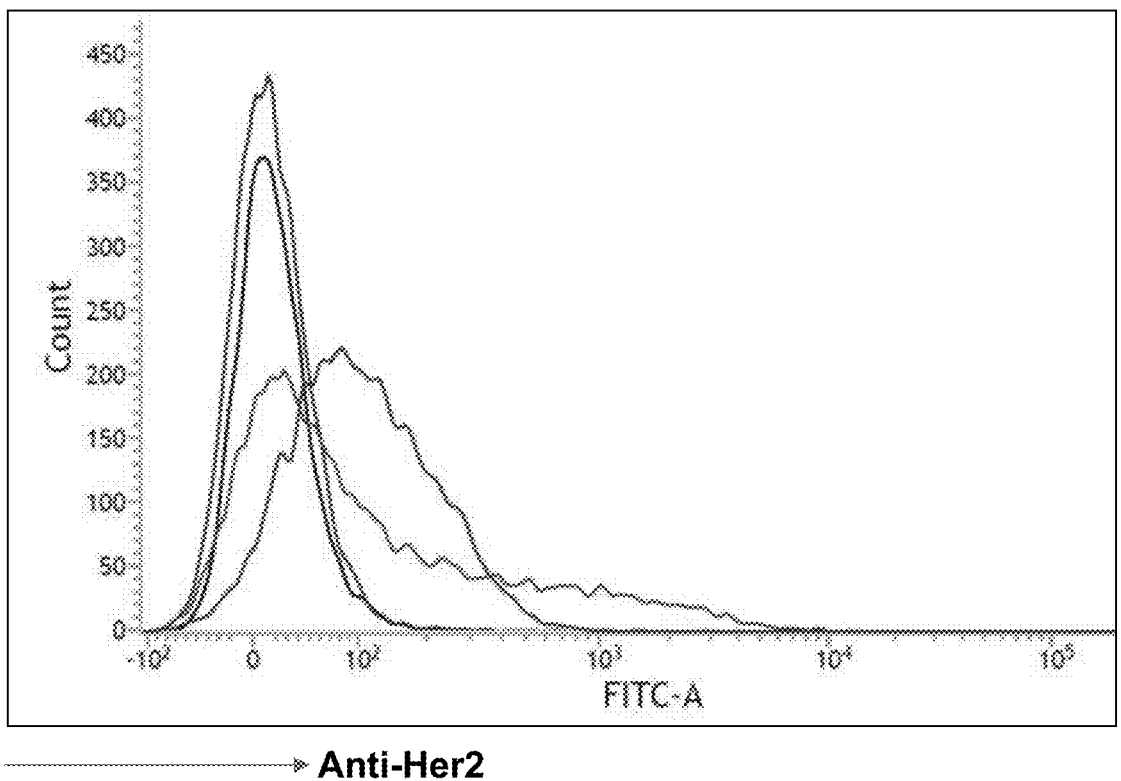
⟶ Anti-Her2
FIG. 11 B
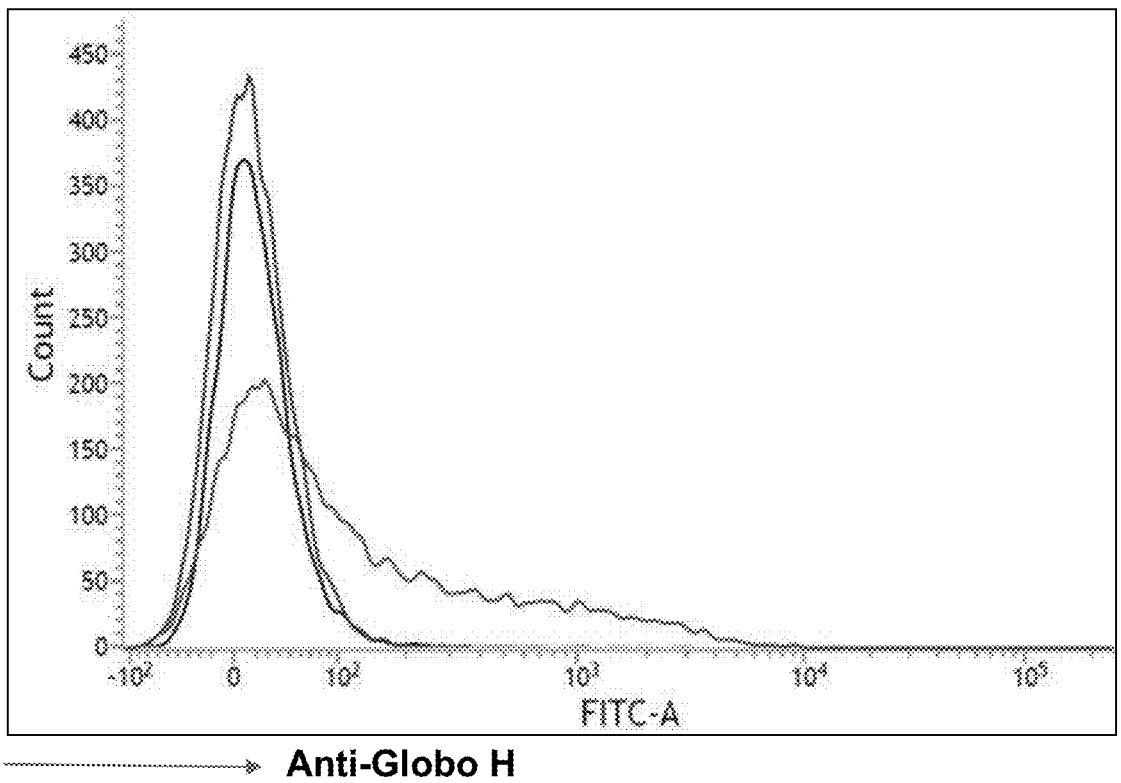
⟶ Anti-Globo H

FIG. 11 C  HCC1428
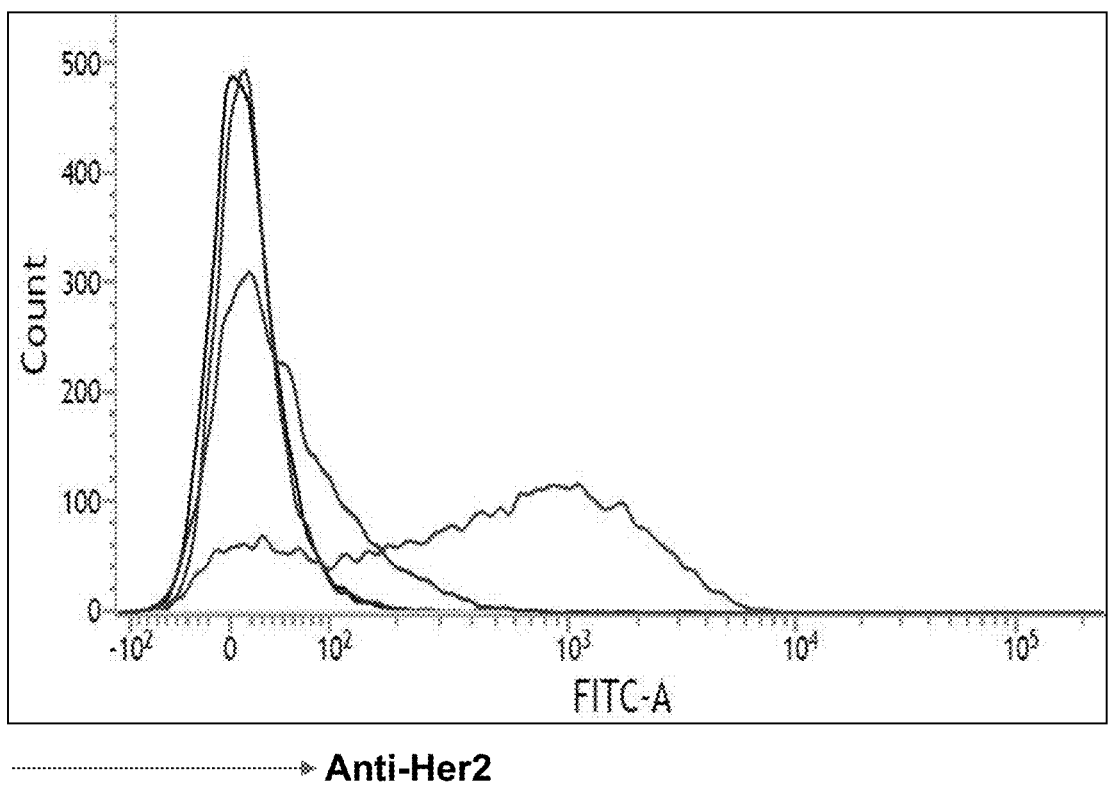
Anti-Her2
FIG. 11 D
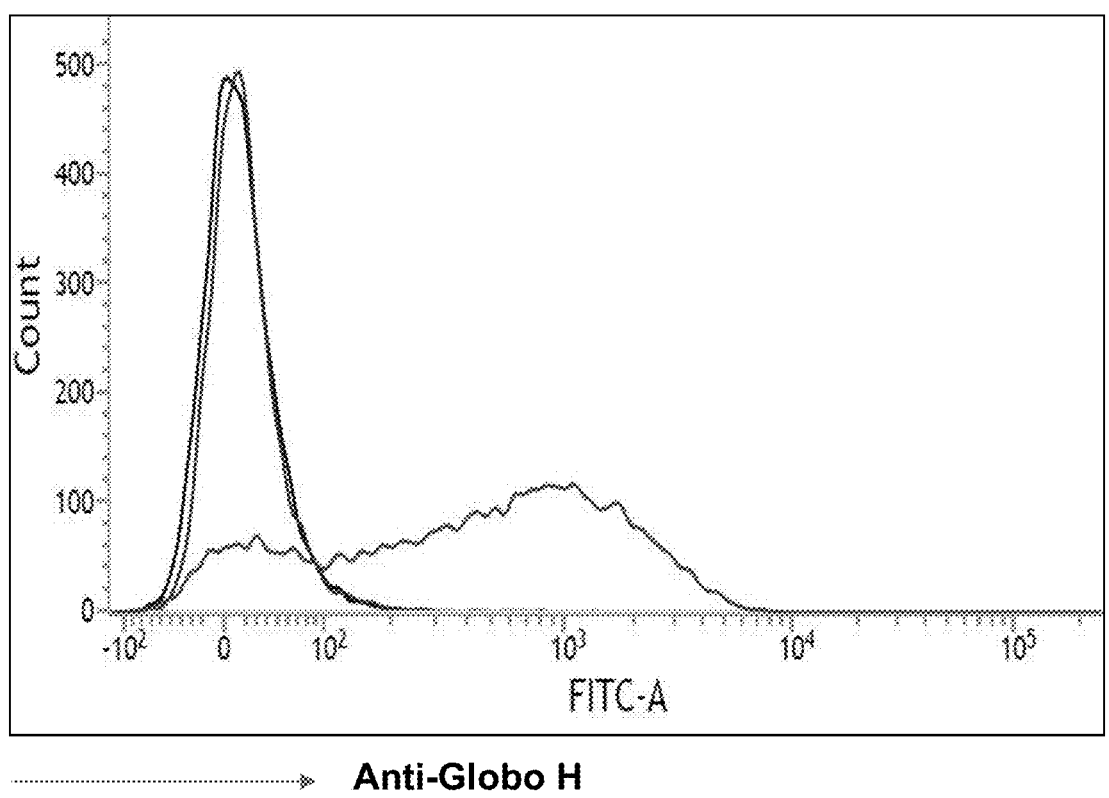
Anti-Globo H

BT474

Anti-Her2

Anti-Globo H

FIG. 11 G Capan-1
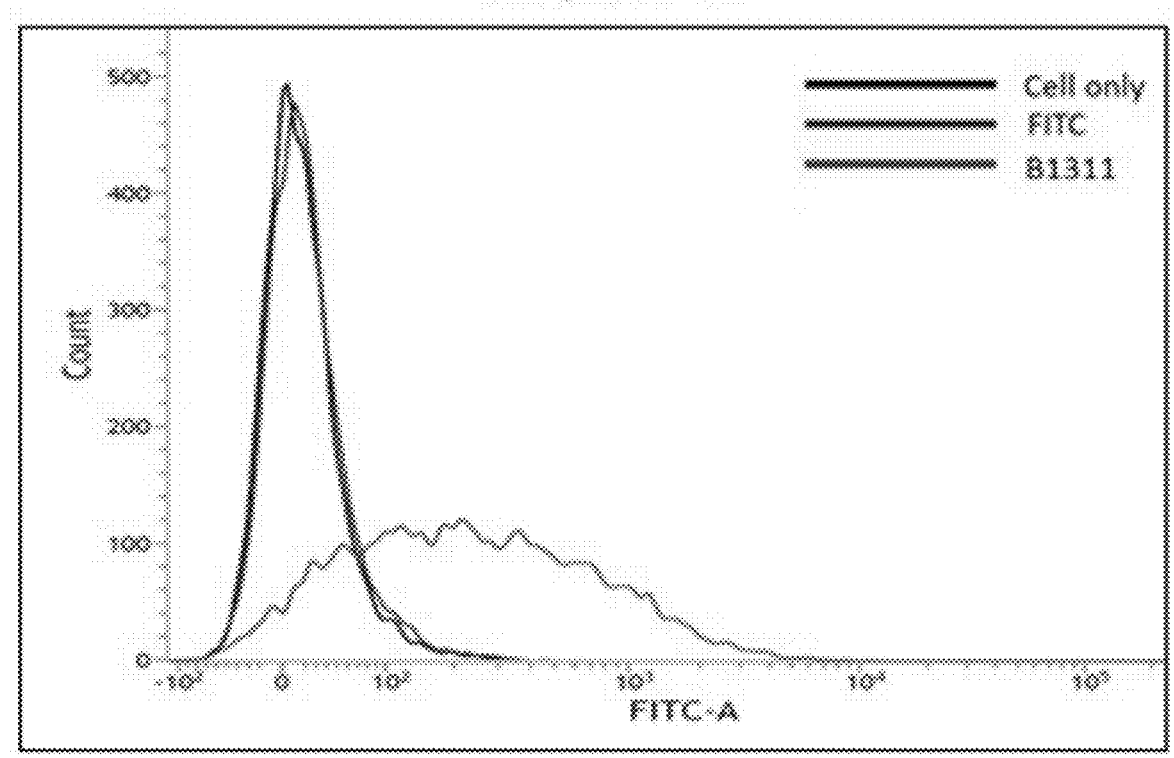
FIG. 11 H A-431
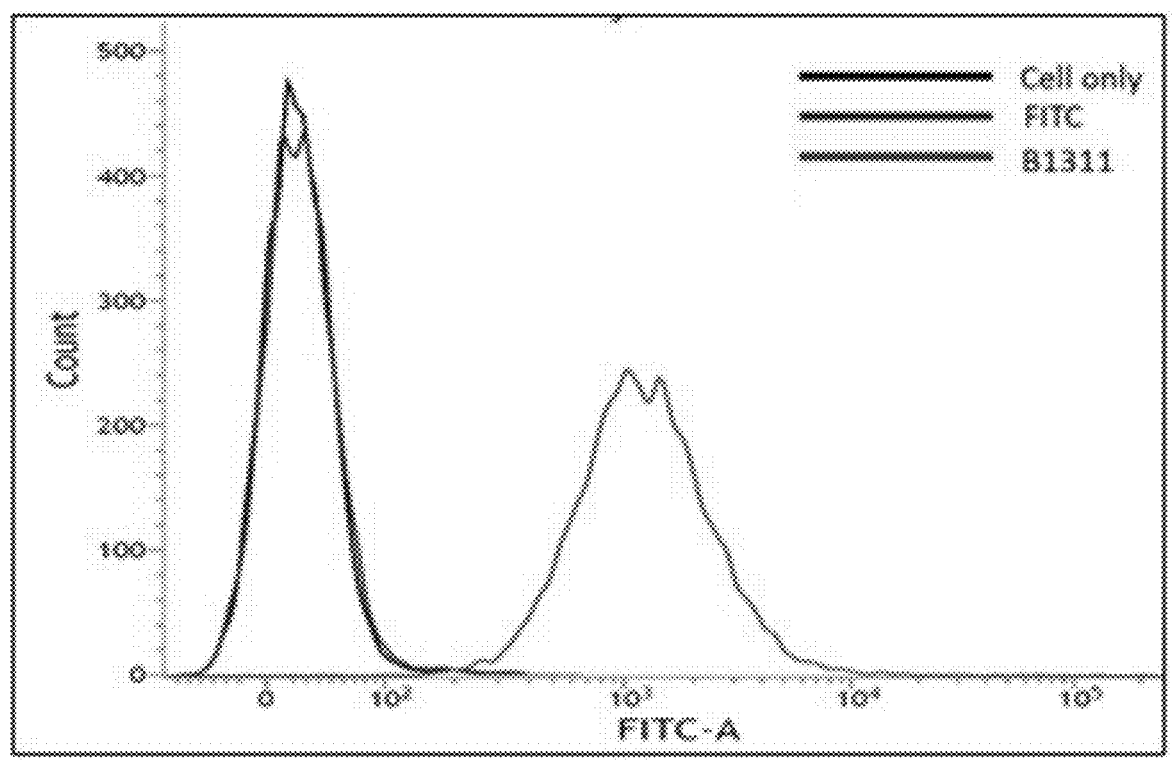

FIG. 17

Gene GBH(VL_Mouse) (SEQ ID NO:1)
GAAATTGTGTTGACCCAGTCTATACCATCCCTGACTGTGTCAGCAGGAGAGAGGGTCACTATCAACTGCAA
GTCCAATCAGAATCTTTTATGGAGTGGAAATCGAAGATACTGTTTAGTTTGGCACCAGTGGAAACCGGGGC
AAAGTCCTAAACCGTTGATCACCTGGGCATCTGATAGGTCTTTTGGAGTCCCTGATCGTTTCATCGGCGGTG
GATCTGTGACAGATTTCACTCTGACCATCAGCAGTGTACGGGCTGAAGATGTGGCAGTTTATTTCTGTCAAC
AACATTTAGACATTCCGTACACGTTCGGAGGGGGGACCAAGTTGGAAATAAAA

Gene GBH(VL_Re2Re2) (SEQ ID NO:2)
GATATTCAGTTGACCCAGTCTATATCCTCCCTGTCCGTGTCAGTGGGAGACAGGGTCACTATCAACTGCAAG
TCCAATCAGAATCTTTTATGGAGTGGAAATCGAAGATACTGTTTAGTTTGGCACCAGTGGAAACCGGGGAA
GAGTCCTAAACCGTTGATCACCTGGGCATCTGATAGGTCTTTTGGAGTCCCTAGCCGTTTCAGCGGCAGCG
GATCTGTGACAGATTTCACTCTGACCATCAGCAGTGTACAGCCCGAAGATTTCGCAGTTTATTTCTGTCAAC
AACATTTAGACATTCCGTACACGTTCGGAGGGGGGACCAAGTTGGAAATAAAA

Gene GBH(VL_B1311) (SEQ ID NO:3)
GACATCCAGCTGACCCAGTCCATCTCCTCCCTGTCCGTGTCCGTGGGCGACAGAGTGACCATCAACTGCAA
GTCCAACCAGAACCTGCTGTGGAGCGGCAACCGGCGGTACACCCTCGTGTGGCATCAGTGGAAGCCCGG
CAAGTCCCCCAAGCCCCTGATCACCTGGGCCTCCGACAGATCTTTCGGCGTGCCCTCCAGATTCTCCGGCTC
CGGCTCTGTGACCGACTTTACCCTGACCATCTCCAGCGTGCAGCCCGAGGACTTCGCCGTGTACTTCTGCC
AGCAGCACCTGGACATCCCTTACACCTTCGGCGGAGGCACCAAGCTGGAAATCAAG

SEQUENCE LISTING

```
<160> NUMBER OF SEQ ID NOS: 23

<210> SEQ ID NO 1
<211> LENGTH: 339
<212> TYPE: DNA
<213> ORGANISM: Mus musculus

<400> SEQUENCE: 1
gaaattgtgt tgacccagtc tataccatcc ctgactgtgt cagcaggaga gagggtcact     60
atcaactgca agtccaatca gaatctttta tggagtggaa atcgaagata ctgtttagtt    120
tggcaccagt ggaaaccggg gcaaagtcct aaaccgttga tcacctgggc atctgatagg    180
tcttttggag tccctgatcg tttcatcggc ggtggatctg tgacagattt cactctgacc    240
atcagcagtg tacgggctga agatgtggca gtttatttct gtcaacaaca tttagacatt    300
ccgtacacgt tcggagggggg gaccaagttg gaaataaaa                          339

<210> SEQ ID NO 2
<211> LENGTH: 339
<212> TYPE: DNA
<213> ORGANISM: Artificial Sequence
<220> FEATURE:
<223> OTHER INFORMATION: Synthetic

<400> SEQUENCE: 2
gatattcagt tgacccagtc tatatcctcc ctgtccgtgt cagtgggaga cagggtcact     60
atcaactgca agtccaatca gaatctttta tggagtggaa atcgaagata ctgtttagtt    120
tggcaccagt ggaaaccggg gaagagtcct aaaccgttga tcacctgggc atctgatagg    180
tcttttggag tccctagccg tttcagcggc agcggatctg tgacagattt cactctgacc    240
atcagcagtg tacagcccga agatttcgca gtttatttct gtcaacaaca tttagacatt    300
ccgtacacgt tcggagggggg gaccaagttg gaaataaaa                          339

<210> SEQ ID NO 3
<211> LENGTH: 339
<212> TYPE: DNA
<213> ORGANISM: Artificial Sequence
<220> FEATURE:
<223> OTHER INFORMATION: Synthetic

<400> SEQUENCE: 3
gacatccagc tgacccagtc catctcctcc ctgtccgtgt ccgtgggcga cagagtgacc     60
atcaactgca agtccaacca gaacctgctg tggagcggca accggcggta caccctcgtg    120
tggcatcagt ggaagcccgg caagtccccc aagcccctga tcacctgggc ctccgacaga    180 tcttttcggcg tgccctccag attctccggc tccggctctg tgaccgactt tacctgacc    240 atctccagcg tgcagcccga ggacttcgcc gtgtacttct gccagcagca cctggacatc    300
ccttacacct tcggcggagg caccaagctg gaaatcaag                           339
```

```
<210> SEQ ID NO 4
<211> LENGTH: 10
<212> TYPE: PRT
<213> ORGANISM: Mus musculus

<400> SEQUENCE: 4

Gly Tyr Ile Ser Ser Asp Gln Ile Leu Asn
1               5                   10

<210> SEQ ID NO 5
<211> LENGTH: 17
<212> TYPE: PRT
<213> ORGANISM: Mus musculus
<220> FEATURE:
<221> NAME/KEY: MISC_FEATURE
<222> LOCATION: (10)..(10)
<223> OTHER INFORMATION: X is any amino acid

<400> SEQUENCE: 5

Arg Ile Tyr Pro Val Thr Gly Val Thr Xaa Tyr Asn His Lys Phe Val
1               5                   10                  15
Gly

<210> SEQ ID NO 6
<211> LENGTH: 6
<212> TYPE: PRT
<213> ORGANISM: Mus musculus

<400> SEQUENCE: 6

Gly Glu Thr Phe Asp Ser
1               5

<210> SEQ ID NO 7
<211> LENGTH: 17
<212> TYPE: PRT
<213> ORGANISM: Mus musculus
<220> FEATURE:
<221> NAME/KEY: MISC_FEATURE
<222> LOCATION: (8)..(8)
<223> OTHER INFORMATION: X at position 8 is F, Y, or W.
<220> FEATURE:
<221> NAME/KEY: MISC_FEATURE
<222> LOCATION: (15)..(15)
<223> OTHER INFORMATION: X at position 15 is C, G, S, or T.

<400> SEQUENCE: 7

Lys Ser Asn Gln Asn Leu Leu Xaa Ser Gly Asn Arg Arg Tyr Xaa Leu
1               5                   10                  15
Val

<210> SEQ ID NO 8
<211> LENGTH: 7
<212> TYPE: PRT
<213> ORGANISM: Mus musculus

<400> SEQUENCE: 8

Trp Ala Ser Asp Arg Ser Phe
1               5

<210> SEQ ID NO 9
<211> LENGTH: 9
<212> TYPE: PRT
<213> ORGANISM: Mus musculus

<400> SEQUENCE: 9

Gln Gln His Leu Asp Ile Pro Tyr Thr
```

<210> SEQ ID NO 10
<211> LENGTH: 115
<212> TYPE: PRT
<213> ORGANISM: Mus musculus

<400> SEQUENCE: 10

Gln Ile Gln Leu His Gln Ser Gly Ile Glu Leu Ala Ser Pro Gly Ser
1               5                   10                  15

Ser Ile Thr Leu Ser Cys Lys Pro Ser Gly Tyr Ile Ser Ser Asp Gln
            20                  25                  30

Ile Leu Asn Trp Val Lys Lys Arg Pro Gly Gln Gly Leu Glu Trp Ile
        35                  40                  45

Gly Arg Ile Tyr Pro Val Thr Gly Val Thr Gln Tyr Asn His Lys Phe
    50                  55                  60

Val Gly Lys Ala Thr Phe Ser Val Asp Arg Ser Ser Asp Thr Val Arg
65                  70                  75                  80

Met Val Met Asn Ser Leu Thr Ser Glu Asp Ser Gly Val Tyr Tyr Cys
                85                  90                  95

Gly Arg Gly Glu Thr Phe Asp Ser Trp Gly Gln Gly Thr Ile Leu Thr
            100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ser Ser Asp Gln
            20                  25                  30

Ile Leu Asn Trp Val Arg Gln Ala Pro Gly Lys Gly Leu Glu Trp Val
        35                  40                  45

Ala Arg Ile Tyr Pro Val Thr Gly Val Thr Gln Tyr Asn His Lys Phe
    50                  55                  60

Val Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Thr Phe Asp Ser Trp Gly Gln Gly Thr Leu Val Thr
            100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: Synthetic

<400> SEQUENCE: 12

Gln Ile Gln Leu Val Glu Ser Gly Gly Gly Leu Val Gln Pro Gly Gly

```
            1               5                   10                  15
        Ser Leu Arg Leu Ser Cys Ala Pro Ser Gly Tyr Ile Ser Ser Asp Gln
                        20                  25                  30

Ile Leu Asn Trp Val Lys Lys Ala Pro Gly Lys Gly Leu Glu Trp Ile
                        35                  40                  45

Gly Arg Ile Tyr Pro Val Thr Gly Val Thr Gln Tyr Asn His Lys Phe
                        50                  55                  60

Val Gly Lys Ala Thr Phe Ser Val Asp Arg Ser Lys Asp Thr Val Tyr
         65                 70                  75                  80

Leu Gln Met Asn Ser Leu Arg Ala Glu Asp Thr Ala Val Tyr Tyr Cys
                        85                  90                  95

Gly Arg Gly Glu Thr Phe Asp Ser Trp Gly Gln Gly Thr Leu Val Thr
                        100                 105                 110

Val Ser Ser
                115

<210> SEQ ID NO 13
<211> LENGTH: 115
<212> TYPE: PRT
<213> ORGANISM: Artificial Sequence
<220> FEATURE:
<223> OTHER INFORMATION: Synthetic

<400> SEQUENCE: 13

Glu Ile Gln Leu Val Gln Ser Gly Gly Gly Leu Ala Gln Pro Gly Gly
         1               5                   10                  15

Ser Ile Arg Leu Ser Cys Ala Pro Ser Gly Tyr Ile Ser Ser Asp Gln
                        20                  25                  30

Ile Leu Asn Trp Val Lys Lys Ala Pro Gly Lys Gly Leu Glu Trp Ile
                        35                  40                  45

Gly Arg Ile Tyr Pro Val Thr Gly Val Thr Gln Tyr Asn His Lys Phe
                        50                  55                  60

Val Gly Lys Ala Thr Phe Ser Val Asp Arg Ser Lys Asp Thr Val Tyr
         65                 70                  75                  80

Met Gln Met Asn Ser Leu Arg Ala Glu Asp Thr Gly Val Tyr Tyr Cys
                        85                  90                  95

Gly Arg Gly Glu Thr Phe Asp Ser Trp Gly Gln Gly Thr Leu Leu Thr
                        100                 105                 110

Val Ser Ser
                115

<210> SEQ ID NO 14
<211> LENGTH: 115
<212> TYPE: PRT
<213> ORGANISM: Artificial Sequence
<220> FEATURE:
<223> OTHER INFORMATION: Synthetic

<400> SEQUENCE: 14

Glu Ile Gln Leu Val Gln Ser Gly Gly Gly Leu Ala Gln Pro Gly Gly
         1               5                   10                  15

Ser Ile Arg Leu Ser Cys Ala Pro Ser Gly Tyr Ile Ser Ser Asp Gln
                        20                  25                  30

Ile Leu Asn Trp Val Lys Lys Ala Pro Gly Lys Gly Leu Glu Trp Ile
                        35                  40                  45

Gly Arg Ile Tyr Pro Val Thr Gly Val Thr Gln Tyr Asn His Lys Phe
                        50                  55                  60
```

```
Val Gly Lys Ala Thr Phe Ser Val Asp Arg Ser Lys Asp Thr Val Tyr
 65                  70                  75                  80

Met Gln Met Asn Ser Leu Arg Ala Glu Asp Thr Gly Val Tyr Tyr Cys
                 85                  90                  95

Gly Arg Gly Glu Thr Phe Asp Ser Trp Gly Gln Gly Thr Leu Leu Thr
            100                 105                 110

Val Ser Ser
        115

<210> SEQ ID NO 15
<211> LENGTH: 114
<212> TYPE: PRT
<213> ORGANISM: Mus musculus

<400> SEQUENCE: 15

Glu Ile Val Leu Thr Gln Ser Ile Pro Ser Leu Thr Val Ser Ala Gly
  1               5                  10                  15

Glu Arg Val Thr Ile Asn Cys Lys Ser Asn Gln Asn Leu Leu Trp Ser
                 20                  25                  30

Gly Asn Arg Arg Tyr Cys Leu Val Trp His Gln Trp Lys Pro Gly Gln
             35                  40                  45

Ser Pro Lys Pro Leu Ile Thr Trp Ala Ser Asp Arg Ser Phe Gly Val
 50                  55                  60

Pro Asp Arg Phe Ile Gly Gly Gly Ser Val Thr Asp Phe Thr Leu Thr
 65                  70                  75                  80

Ile Ser Ser Val Arg Ala Glu Asp Val Ala Val Tyr Phe Cys Gln Gln
                 85                  90                  95

His Leu Asp Ile Pro Tyr Thr Phe Gly Gly Gly Thr Lys Leu Glu Ile
             100                 105                 110

Lys Arg

<210> SEQ ID NO 16
<211> LENGTH: 114
<212> TYPE: PRT
<213> ORGANISM: Artificial Sequence
<220> FEATURE:
<223> OTHER INFORMATION: Synthetic

<400> SEQUENCE: 16

Asp Ile Gln Met Thr Gln Ser Pro Ser Ser Leu Ser Ala Ser Val Gly
  1               5                  10                  15

Asp Arg Val Thr Ile Thr Cys Lys Ser Asn Gln Asn Leu Leu Trp Ser
                 20                  25                  30

Gly Asn Arg Arg Tyr Cys Leu Val Trp Tyr Gln Gln Lys Pro Gly Lys
             35                  40                  45

Ala Pro Lys Leu Leu Ile Tyr Trp Ala Ser Asp Arg Ser Phe Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Leu Asp Ile Pro Tyr Thr Phe Gly Gln Gly Thr Lys Val Glu Ile
             100                 105                 110

Lys Arg

<210> SEQ ID NO 17
<211> LENGTH: 114
```

<212> TYPE: PRT
<213> ORGANISM: Artificial Sequence
<220> FEATURE:
<223> OTHER INFORMATION: Synthetic

<400> SEQUENCE: 17

Glu Ile Val Leu Thr Gln Ser Pro Ser Ser Leu Ser Ala Ser Val Gly
1               5                   10                  15

Asp Arg Val Thr Ile Asn Cys Lys Ser Asn Gln Asn Leu Leu Trp Ser
            20                  25                  30

Gly Asn Arg Arg Tyr Cys Leu Val Trp His Gln Trp Lys Pro Gly Lys
        35                  40                  45

Ala Pro Lys Pro Leu Ile Thr Trp Ala Ser Asp Arg Ser Phe Gly Val
    50                  55                  60

Pro Ser Arg Phe Ser Gly Ser Gly Ser Val Thr Asp Phe Thr Leu Thr
65                  70                  75                  80

Ile Ser Ser Leu Gln Pro Glu Asp Phe Ala Thr Tyr Phe Cys Gln Gln
                85                  90                  95

His Leu Asp Ile Pro Tyr Thr Phe Gly Gln Gly Thr Lys Val Glu Ile
            100                 105                 110

Lys Arg

<210> SEQ ID NO 18
<211> LENGTH: 114
<212> TYPE: PRT
<213> ORGANISM: Artificial Sequence
<220> FEATURE:
<223> OTHER INFORMATION: Synthetic

<400> SEQUENCE: 18

Asp Ile Gln Leu Thr Gln Ser Ile Ser Ser Leu Ser Val Ser Val Gly
1               5                   10                  15

Asp Arg Val Thr Ile Asn Cys Lys Ser Asn Gln Asn Leu Leu Trp Ser
            20                  25                  30

Gly Asn Arg Arg Tyr Cys Leu Val Trp His Gln Trp Lys Pro Gly Lys
        35                  40                  45

Ser Pro Lys Pro Leu Ile Thr Trp Ala Ser Asp Arg Ser Phe Gly Val
    50                  55                  60

Pro Ser Arg Phe Ser Gly Ser Gly Ser Val Thr Asp Phe Thr Leu Thr
65                  70                  75                  80

Ile Ser Ser Val Gln Pro Glu Asp Phe Ala Val Tyr Phe Cys Gln Gln
                85                  90                  95

His Leu Asp Ile Pro Tyr Thr Phe Gly Gly Gly Thr Lys Leu Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic

<400> SEQUENCE: 19

Asp Ile Gln Leu Thr Gln Ser Ile Ser Ser Leu Ser Val Ser Val Gly
1               5                   10                  15

Asp Arg Val Thr Ile Asn Cys Lys Ser Asn Gln Asn Leu Leu Trp Ser
            20                  25                  30

Gly Asn Arg Arg Tyr Cys Leu Val Trp His Gln Trp Lys Pro Gly Lys
            35                  40                  45

Ser Pro Lys Pro Leu Ile Thr Trp Ala Ser Asp Arg Ser Phe Gly Val
 50                  55                  60

Pro Ser Arg Phe Ser Gly Ser Gly Ser Val Thr Asp Phe Thr Leu Thr
 65                  70                  75                  80

Ile Ser Ser Val Gln Pro Glu Asp Phe Ala Val Tyr Phe Cys Gln Gln
                85                  90                  95

His Leu Asp Ile Pro Tyr Thr Phe Gly Gly Gly Thr Lys Leu Glu Ile
                100                 105                 110

Lys Arg

<210> SEQ ID NO 20
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (59)..(59)
<223> OTHER INFORMATION: X is any amino acid

<400> SEQUENCE: 20

Glu Ile Gln Leu Val Gln Ser Gly Gly Gly Leu Ala Gln Pro Gly Gly
 1               5                  10                  15

Ser Ile Arg Leu Ser Cys Ala Pro Ser Gly Tyr Ile Ser Ser Asp Gln
            20                  25                  30

Ile Leu Asn Trp Val Lys Lys Ala Pro Gly Lys Gly Leu Glu Trp Ile
            35                  40                  45

Gly Arg Ile Tyr Pro Val Thr Gly Val Thr Xaa Tyr Asn His Lys Phe
 50                  55                  60

Val Gly Lys Ala Thr Phe Ser Val Asp Arg Ser Lys Asp Thr Val Tyr
 65                  70                  75                  80

Met Gln Met Asn Ser Leu Arg Ala Glu Asp Thr Gly Val Tyr Tyr Cys
                85                  90                  95

Gly Arg Gly Glu Thr Phe Asp Ser Trp Gly Gln Gly Thr Leu Leu Thr
                100                 105                 110

Val Ser Ser
        115

<210> SEQ ID NO 21
<211> LENGTH: 115
<212> TYPE: PRT
<213> ORGANISM: Artificial Sequence
<220> FEATURE:
<223> OTHER INFORMATION: Synthetic

<400> SEQUENCE: 21

Glu Ile Gln Leu Val Gln Ser Gly Gly Gly Leu Ala Gln Pro Gly Gly
 1               5                  10                  15

Ser Ile Arg Leu Ser Cys Ala Pro Ser Gly Tyr Ile Ser Ser Asp Gln
            20                  25                  30

Ile Leu Asn Trp Val Lys Lys Ala Pro Gly Lys Gly Leu Glu Trp Ile
            35                  40                  45

Gly Arg Ile Tyr Pro Val Thr Gly Val Thr Gln Tyr Asn His Lys Phe
 50                  55                  60

Val Gly Lys Ala Thr Phe Ser Val Asp Arg Ser Lys Asp Thr Val Tyr
 65                  70                  75                  80

```
Met Gln Met Asn Ser Leu Arg Ala Glu Asp Thr Gly Val Tyr Tyr Cys
             85                  90                  95

Gly Arg Gly Glu Thr Phe Asp Ser Trp Gly Gln Gly Thr Leu Leu Thr
        100                 105                 110

Val Ser Ser
        115

<210> SEQ ID NO 22
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is W, Y, or F.
<220> FEATURE:
<221> NAME/KEY: MISC_FEATURE
<222> LOCATION: (38)..(38)
<223> OTHER INFORMATION: X is C, G, S, or T.

<400> SEQUENCE: 22

Asp Ile Gln Leu Thr Gln Ser Ile Ser Ser Leu Ser Val Ser Val Gly
1               5                   10                  15

Asp Arg Val Thr Ile Asn Cys Lys Ser Asn Gln Asn Leu Leu Xaa Ser
            20                  25                  30

Gly Asn Arg Arg Tyr Xaa Leu Val Trp His Gln Trp Lys Pro Gly Lys
        35                  40                  45

Ser Pro Lys Pro Leu Ile Thr Trp Ala Ser Asp Arg Ser Phe Gly Val
    50                  55                  60

Pro Ser Arg Phe Ser Gly Ser Gly Ser Val Thr Asp Phe Thr Leu Thr
65                  70                  75                  80

Ile Ser Ser Val Gln Pro Glu Asp Phe Ala Val Tyr Phe Cys Gln Gln
                85                  90                  95

His Leu Asp Ile Pro Tyr Thr Phe Gly Gly Gly Thr Lys Leu Glu Ile
            100                 105                 110

Lys Arg

<210> SEQ ID NO 23
<211> LENGTH: 114
<212> TYPE: PRT
<213> ORGANISM: Artificial Sequence
<220> FEATURE:
<223> OTHER INFORMATION: Synthetic

<400> SEQUENCE: 23

Asp Ile Gln Leu Thr Gln Ser Ile Ser Ser Leu Ser Val Ser Val Gly
1               5                   10                  15

Asp Arg Val Thr Ile Asn Cys Lys Ser Asn Gln Asn Leu Leu Trp Ser
            20                  25                  30

Gly Asn Arg Arg Tyr Thr Leu Val Trp His Gln Trp Lys Pro Gly Lys
        35                  40                  45

Ser Pro Lys Pro Leu Ile Thr Trp Ala Ser Asp Arg Ser Phe Gly Val
    50                  55                  60

Pro Ser Arg Phe Ser Gly Ser Gly Ser Val Thr Asp Phe Thr Leu Thr
65                  70                  75                  80

Ile Ser Ser Val Gln Pro Glu Asp Phe Ala Val Tyr Phe Cys Gln Gln
                85                  90                  95
```

```
His Leu Asp Ile Pro Tyr Thr Phe Gly Gly Thr Lys Leu Glu Ile
            100                 105                 110
Lys Arg
```

HUMANIZED ANTIBODIES AGAINST GLOBO H AND USES THEREOF IN CANCER TREATMENTS

FIELD OF THE INVENTION

The present invention relates to humanized antibodies that bind specifically to Globo H. The present invention also relates to methods for treating and/or diagnosing cancer using these antibodies.

BACKGROUND OF THE INVENTION

Globo H (Fuc-α1,2-Gal-β1,3-GalNAc-β1,3-Gal-α1,4-Gal-β1,4-Glc-β1,1-Cer) is a hexasaccharide, belonging to a large number of tumor-associated carbohydrate antigens that are overexpressed on the surface of various epithelial cancer cells, including breast, colon, ovarian, pancreatic, lung, and prostate cancer cells. In addition to Globo H, other known carbohydrate antigens include Tn (GalNAc-α-O-Ser/Thr), Sialyl Tn (Neu5Ac-α2,6-GalNAc-α-O-Ser/Thr, STn), GD2, GD3, GD3L, fucosyl-GM1, Lewis antigens (Lex, Ley, Lea, sialyl Lex, sialyl Lea), TF (Gal-β1,3-GalNAc-α-O-Ser/Thr) and are also used as target antigens for cancer immunotherapy (Susan F Slovin et al, Carbohydrate Vaccines as Immunotherapy for Cancer, Immunology and Cell Biology (2005) 83, 418-428; Zhongwu Guo and Qianli Wang, Recent Development in Carbohydrate-Based Cancer Vaccines, Curr. Opin. Chem. Biol. 2009 December; 13(5-6): 608-617; Therese Buskas et al., Immunotherapy for Cancer: Synthetic Carbohydrate-based Vaccines, Chem. Commun. (Comb). 2009 Sep. 28; (36): 5335-5349).

However, most carbohydrate antigens are often tolerated by the immune system, and consequently, the immunogenicity induced by them is limited. Further, the production of antibody against a specific immunogen typically involves cooperative interactions between two types of lymphocytes, i.e., B-cells and helper T-cells. Globo H alone cannot activate helper T-cells, which also attributes to the poor immunogenicity of Globo H. Accordingly, immunization with Globo H alone often results in low titers of immunoglobulin M (IgM) and failure to class switch to immunoglobulin G (IgG), as well as ineffective antibody affinity maturation.

Recently, it has been demonstrated that with addition of suitable adjuvants, antibodies against Globo H can be induced, including class switching from IgM to IgG. Thus, Globo H is a promising therapeutic target for cancer vaccination. This approach has been in clinical trials at various stages against various cancers, including breast cancer, ovarian cancer, prostate cancer, and lung cancer.

While antibodies against Globo H have been shown to be promising in cancer diagnosis and therapy, better anti-Globo H antibodies are still needed.

SUMMARY OF THE INVENTION

Embodiments of the invention relate to humanized Globo H antibodies that specifically bind Globo H, as well as methods using such antibodies in the diagnosis and/or treatment of cancers. By specifically binding Globo H, antibodies of the invention may be used to diagnose and/or treat cancers that overexpress Globo H, including various epithelial cancers.

One aspect of the invention relates to humanized anti-Globo H antibodies. In accordance with one embodiment of the invention, a humanized anti-Globo H antibody, or an scFv or Fab fragment thereof, comprises a heavy-chain variable domain having three complementary regions consisting of HCDR1, HCDR2, and HCDR3 and a light-chain variable domain having three complementary regions consisting of LCDR1, LCDR2, and LCDR3, wherein the sequence of HCDR1 is GYISSDQILN (SEQ ID NO:4), the sequence of HCDR2 is RIYPVTGVTQYXHKFVG (SEQ ID NO:5, wherein X is any amino acid), and the sequence of HCDR3 is GETFDS (SEQ ID NO:6), wherein the sequence of LCDR1 is KSNQNLLX'SGNRRYZLV (SEQ ID NO:7, wherein X' is F, Y, or W, and Z is C, G, S or T), the sequence of LCDR2 is WASDRSF (SEQ ID NO:8), and the sequence of LCDR3 is QQHLDIPYT (SEQ ID NO:9).

In accordance with some embodiments of the invention, the X in SEQ ID NO:5 is asparagine or glutamine. In accordance with some embodiments of the invention, the X' in SEQ ID NO:7 is tryptophan. In accordance with some embodiments of the invention, the Z in SEQ ID NO:7 is serine or threonine.

One aspect of the invention relates to methods for diagnosing, or preventing and/or treating cancers. A method in accordance with one embodiment of the invention comprises administering an effective amount of an anti-Globo H antibody to a subject in need thereof. An effective amount is that can achieve the desired treatment outcome. One skilled in the art would appreciate that an effective amount may vary based on patient's age, sex, body weight, conditions, etc. Such effective amounts are routinely determined based on the patient and conditions. One skilled in the art would be able to determine the effective amount without undue experimentation. The cancer is breast, colon, ovarian, pancreatic, lung, liver, or prostate cancer.

BRIEF DESCRIPTION OF THE DRAWINGS

FIG. 8A shows primary sequence alignments of the framework regions of the $V_H$ segments of various anti-Globo H antibodies (GBH): mouse GBH (M), humanized GBH (H), back mutated humanized GBH (B1), further refined GBH (Re2), and GBH (B11).

FIG. 8B shows primary sequence alignments of the framework regions of the $V_L$ segments of various anti-Globo H antibodies (GBH): mouse GBH (M), humanized GBH (H), back mutated humanized GBH (B1), further refined GBH (Re2), and GBH (B13).

FIG. 9A shows the sequences of HCDR1, HCDR2, and HCD3 for a consensus clone GBH (C) based on results from alanine scanning and various amino acid replacements in the CDR regions. Also shown is an exemplary clone GBH (B11), which contains glutamine (Q) at the non-critical residue X in HCDR2.

FIG. 9B shows the sequences of LCDR1, LCDR2, and LCDR3 for a consensus clone GBH (C) based on results from alanine scanning and various amino acid replacements in the CDR regions. Also shown is an exemplary clone GBH (B13), which contains tryptophan (W) at the aromatic residue X and threonine (T) at the flexible residue Z in LCDR1.

FIG. 11A shows that MCF7 breast cancer cells express Her2 antigen, and FIG. 11B shows that MCF7 breast cancer cells express Globo H antigen. FIG. 11C shows that HCC1428 hepatoma cells express Her2 antigen, and FIG. 11D shows that HCC1428 hepatoma cells express Globo H antigen. FIG. 11E shows that BT474 breast cancer cells express Her2 antigen, but not Globo H (FIG. 11F). Similarly, FIG. 11G shows that Capan-1 pancreatic cancer cells express Globo H. FIG. 11H shows that A-431 squamous carcinoma cells express Globo H. FIG. 11I shows that NCI-N87 gastric cancer cells express Globo H. FIG. 11J shows that HT-29 colorectal cancer cells express low level of Globo H.

FIG. 12A shows results of MCF7 cells. FIG. 12B shows results of HCC1428 cells. FIG. 12C shows results of BT474 cells. FIG. 12D shows the results of Capan-1. FIG. 12E shows the results of NCI-N87. FIG. 12F shows the results of A431. These results show that expression of Glob H is required for the ADCC mediated by anti-Globo H antibodies.

FIG. 13A shows results of MCF7 cells. FIG. 13B shows results of HCC1428 cells. FIG. 13C shows results of BT474 cells. FIG. 13D shows the results of Capan-1 cells. FIG. 13E shows the results of NCI-N87. These results show that expression of Glob H is required for the CDC mediated by anti-Globo H antibodies.

FIG. 17 shows that sequences (SEQ ID NO:1; SEQ ID NO:2, and SEQ ID NO:3) of GBH light-chain variable domains of various anti-Globo H antibodies.

DEFINITIONS

Figure 1:
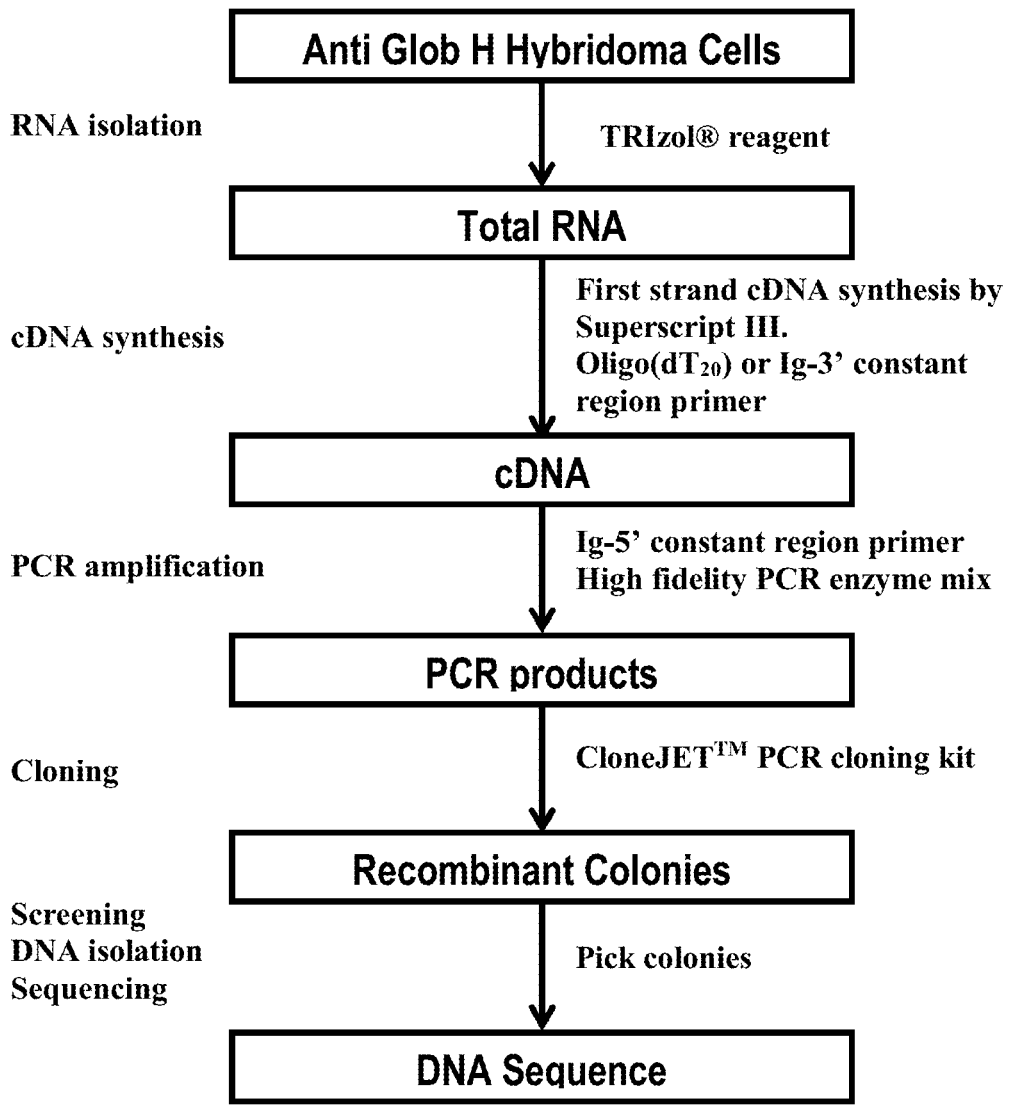
FIG. 1 shows a flowchart illustrating a method for obtaining clones of antibodies against Globo H.

Unless otherwise defined, scientific and technical terms used herein shall have the meanings that are commonly understood by those of ordinary skill in the art. Furthermore, unless otherwise required by context, singular terms shall include pluralities and plural terms shall include the singular. Generally, nomenclatures used in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular Cloning: A Laboratory Manual (3rd ed., Cold Spring Harbor Laboratory Press, Cold Spring Harbor, N.Y. (2001)), which is incorporated herein by reference.

As used herein, the term "chimeric antibody" refers to antibodies that contain sequences from more than one source (e.g., species).

As used herein, the term "humanized antibody" refers to an antibody in which minimal portions of a non-human antibody are introduced into an otherwise human antibody.

As used herein, the term "human antibody" refers to an antibody in which substantially every part of the protein is substantially non-immunogenic in humans, with only minor sequence changes or variations.

As used herein, the term "antigen-binding fragment" refers to a fragment of an antibody that retain the ability to bind the antigen. Such antigen-binding fragments may include scFv, Fab, F(ab')$_2$, or the like.

The term "CDR region" or "CDR" is intended to indicate the hypervariable regions of the heavy or light chains of the immunoglobulin as defined by Kabat et al., 1991 (Kabat, E. A. et al., (1991) *Sequences of Proteins of Immunological Interest*, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for binding the antigen or the epitope which it recognizes.

The term a "set of CDRs" referred to herein comprises CDR1, CDR2 and CDR3. Thus, a set of HCDRs refers to HCDR1, HCDR2 and HCDR3 (HCDR refers to a heavy chain CDR), and a set of LCDRs refers to LCDR1, LCDR2 and LCDR3 (LCDR refers to a light chain CDR). Unless otherwise stated, a "set of CDRs" may include HCDRs and/or LCDRs.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. It should be appreciated that there can be differing regions of homology within two orthologous sequences. For example, the functional regions of mouse and human orthologues may have a higher degree of homology than non-functional regions.

An antigen binding site is generally formed by the variable heavy (VH) and variable light (VL) immunoglobulin domains, with the antigen-binding interface formed by six surface polypeptide loops, termed complementarity determining regions (CDRs). There are three CDRs in each VH (HCDR1, HCDR2, HCDR3) and in each VL (LCDR1, LCDR2, LCDR3), together with framework regions (FRs).

An antibody antigen-binding site composed of a VH domain and a VL domain is typically formed by six loops of polypeptide: three from the light chain variable domain (VL) and three from the heavy chain variable domain (VH). Analysis of antibodies of known atomic structure can elucidate relationships between the sequence and three-dimensional structure of antibody combining sites.

The study of sequence-structure relationship can be used to predict those residues in an antibody with a known sequence but unknown three-dimensional structure, which are important in maintaining the three-dimensional structure of its CDR loops and hence maintain binding specificity. In a structural approach, a model can be created of the antibody molecule using any freely available or commercial package, such as WAM. A protein visualization and analysis software package, such as Insight II (Accelrys, Inc.) or Deep View may then be used to evaluate possible substitutions at each position in the CDR. This information may then be used to make substitutions likely to have a minimal or beneficial effect on activity.

The techniques for making amino acid substitutions within the sequences of CDRs and antibody VH or VL domains are available in the art.

DETAILED DESCRIPTION

Embodiments of the invention relate to anti-Globo H antibodies and their uses in the diagnosis and treatment of cancers. The practice of the present invention will employ technologies comprising conventional techniques of cell biology, cell culture, antibody technology, and genetic engineering, which are within the ordinary skills of the art.

The following examples illustrate the development of humanized anti-Globo H antibodies and their uses in the diagnosis and treatment of cancers. One skilled in the art would appreciate that these examples are for illustration only and are not meant to limit the scope of the invention.

As noted above, Globo H is a hexasaccharide and is overexpressed on the surface of epithelial cancer cells, including breast, colon, ovarian, pancreatic, lung, and prostate cancer cells. Antibodies against Globo H have been shown to be useful in the treatment and diagnosis of such cancers. To be used on patients, the antibodies should have minimal or no adverse effects, such as no undesired immunological responses. Embodiments of the invention relate to humanized anti-Globo H antibodies. These humanized antibodies have good binding efficiencies and have no or minimal undesired immunological responses.

In accordance with embodiments of the invention, a general method for the generation of humanized anti-Globo H antibodies include obtaining a hybridoma producing a monoclonal antibody against Globo H, obtaining the CDR sequences from the hybridoma, and cloning the CDR sequences into human framework sequences to produce humanized antibodies. The humanized antibodies may be further optimized, for example to improve the sequences in the framework region and/or the CDR sequences. FIG. 1 shows a flowchart outlining a method in accordance with one embodiment of the invention for obtaining a humanized anti-Globo H antibody.

Methods for various procedures are known in the art. The following specific examples illustrate exemplary embodiments. However, one skilled in the art would appreciate that modifications or variations are possible without departing from the scope of the invention.

Molecular Cloning of V Regions of Anti-Globo H Antibodies

First, a hybridoma of anti-Globo H (e.g., mouse GBH hybridoma) was generated. Such a hybridoma may be generated with standard protocols for the production of monoclonal antibodies. The total RNA of the hybridoma was then isolated, for example using the TRIzol® reagent. Then, cDNA was synthesized from the total RNA, for example using a first strand cDNA synthesis kit (Superscript III) and an oligo($dT_{20}$) primer or an Ig-3' constant region primer.

Heavy and light chain variable regions of the immunoglobulin genes were then cloned from the cDNA. For example, the VH and VL variable regions of the anti-Globo H mAb were amplified from mouse GBH hybridoma cDNAs by PCR, using a mouse Ig-5' primer set (Novagen). The PCR products may be cloned directly into a suitable vector (e.g., a pJET1.2 vector) using CloneJet™ PCR Cloning Kit (Ferments). The pJET1.2 vector contains lethal insertions and will survive the selection conditions only when the desired gene is cloned into this lethal region. This facilitates the selection of recombinant colonies. Finally, the recombinant colonies were screened for the desired clones, the DNAs of those clones were isolated and sequenced. The immunoglobulin (IG) nucleotide sequences may be analyzed at the international ImMunoGeneTics information system (IGMT) website.

Antibody Expression and Purification

For antibody production, the isolated clones may be expressed in any suitable cells. As an example, F293 cells (Life technologies) were transfected with the anti-Globo H mAb expressing plasmid and cultured for 7 days. The anti-Globo H antibody was purified from the culture medium using a protein A affinity column (GE). Protein concentrations may be determined with a Bio-Rad protein assay kit and analyzed with 12% SDS-PAGE, using procedures known in the art or according to the manufacturer's instructions.

ELISA Assay

Antibody affinities may be assessed with any suitable methods known in the art, such as ELISA or Biacore. For example, Globo H—NH2 (Oligotech), diluted in sodium carbonate buffer (pH9.5), was coated on a 96-well plate at 4° C. overnight. After blocking (e.g., with BSA), two-fold serial diluted anti-Globo H antibodies were added to the wells and incubated at 37° C. for 2 hr. After binding, Goat anti-human IgG-HRP (1:15000) was added and incubated at 37° C. for 1 hr. Then, 3,3',5,5'-Tetramethylbenzidine (TMB) substrate was used to develop colors and the reaction was stopped by addition of 1N $H_2SO_4$. The extents of antigen-antibody bindings were determined by reading the plates, i.e., by measuring absorbance at 450-655 nm, using an ELISA reader (BioRad Model 680). Data may be analyzed using any suitable software, such as the GraphPad Prism 5 software.

Humanization of Anti-Globo H Antibody

Figure 2:
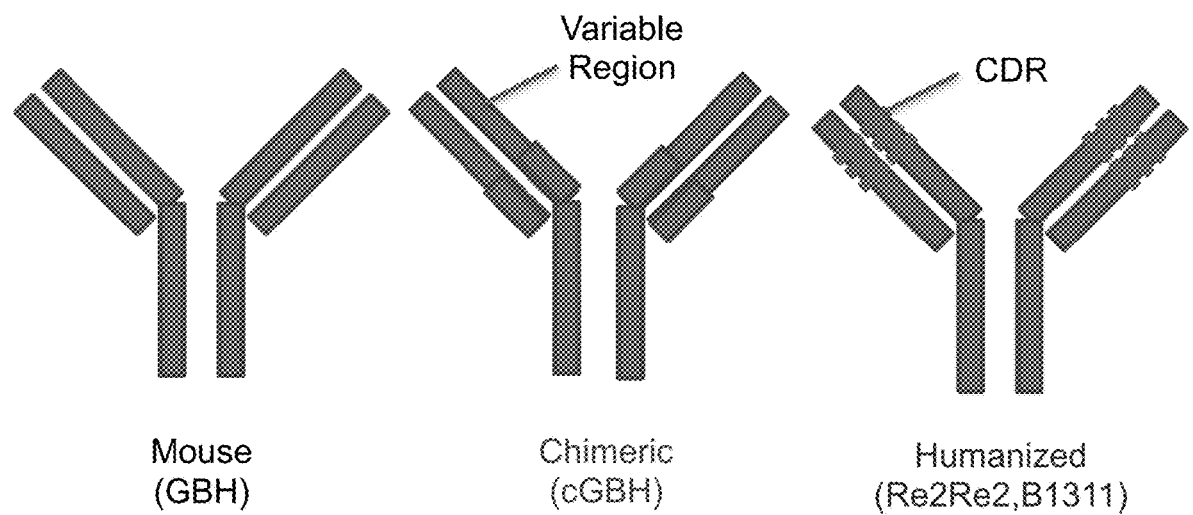
FIG. 2 shows a schematic of mouse anti-Globo H antibody, a chimeric anti-Globo H antibody, and a humanized anti-Globo H antibody.

Embodiments of the invention relate to humanization of anti-Globo H antibodies. FIG. 2 shows schematic illustration of a chimeric antibody and a humanized antibody. Chimeric antibody is one with the variable regions and the constant region from different sources (e.g., different species). For example, the variable regions of a mouse anti-Globo H antibody cloned from the above described procedures may be grafted on the constant regions of a human antibody to generate a chimeric antibody.

Figure 3:
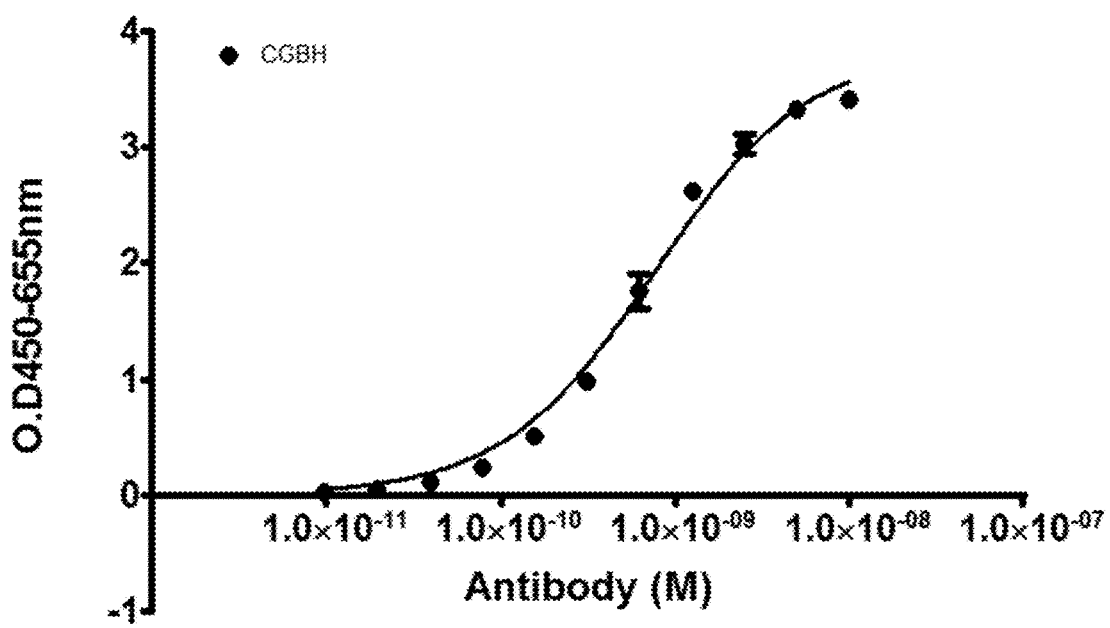
FIG. 3 shows binding curve of a chimeric anti-Globo H antibody, illustrating high affinity of binding with a binding constant of sub-nano molar.

FIG. 3 shows a binding assay of a chimeric antibody in accordance with one embodiment of the invention. The binding assay was performed with ELISA as described above. Form this binding curve, one can estimate that the binding constant of this chimeric antibody is better than 1.0 nM, indicating grafting the variable domains of antibody onto the constant domains of human antibody would not compromise the binding as one would expect.

Referring to FIG. 2, a humanized antibody contains the CDRs from one species and the framework regions and the constant regions from a human immunoglobulin. An exemplary process for generating a humanized antibody may be as follows.

1) Selection of Human V Region Framework

Frameworks from human immunoglobulins with highest degrees of homology with the framework regions in the above-cloned variable regions from mouse were selected from the IMGT database. Based on the homology comparison, a framework for heavy chain in the VH3 subgroup and a framework for the light chain in the Vk1 subgroup, respectively, were selected for the humanized anti-Globo H mAb (GBH).

2) Construction of CDR Grafted Anti-Globo H Antibodies

The human frameworks (VL κ subgroup I and VH subgroup III) with the six complete murine CDR sequences were assembled by PCR and then sub-cloned into an antibody expression vector. Any suitable vectors known in the art may be used. This would generate hybrid variable regions (VH and VL).

3) Back Mutation

Grafting of CDR onto frameworks results in variable domains (VH and VL) from different sources. Such heterologous domains may not have the optimal sequences. Therefore, affinities of the antibodies may not be the best. To improve the binding affinity, some amino acids may be mutated back to the other species.

Figure 4:
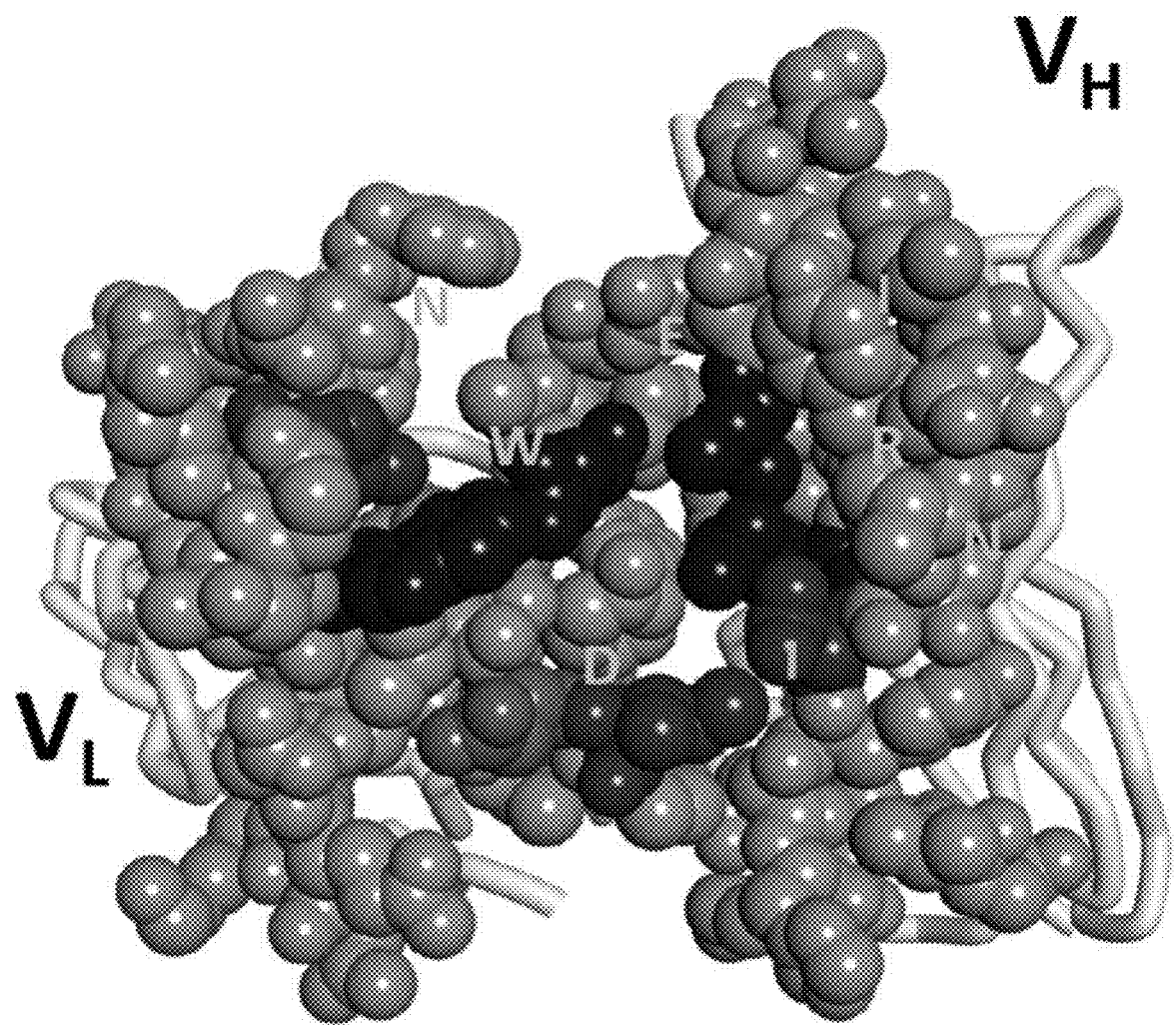
FIG. 4 shows a model of the variable domains of an anti-Globo H antibody used in computer modeling.

As shown in FIG. 4, critical amino acid residues that may impact antibody bindings may be analyzed by computer modeling. The modeling may examine (for example within a 5 Å region) the upper core region and the interface area. In the modeling, one may also apply prior knowledge based on successful cases. Based on the modeling, amino acid substitutions may be performed, for example, to replace the amino acid residues with the corresponding amino acid residues in the original species (i.e., back mutation). Then, the mutant antibodies may be assessed for their bindings to select for improved antibodies.

Clone GBH(B1) was thus selected from the first run back mutation. Clone GBH(Re1) and GBH(Re2) were generated, based on the B1 clone, from further mutations with the following additional considerations: (i) to avoid most structurally conserved strands of the Fv β-barrel; (ii) to rank resurfacing site (mouse amino acid) by relative high surface accessibility (e.g., greater than 30%); and (iii) to classify framework generally reported risk sites.

Figure 5:
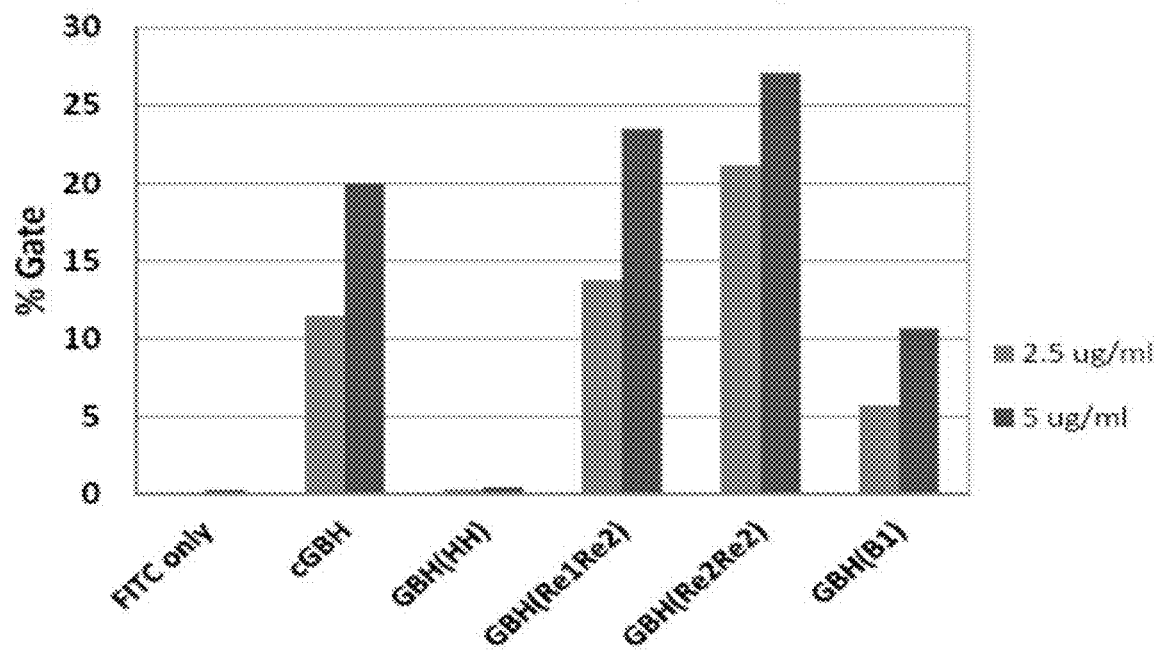
FIG. 5 shows results of various anti-Globo H antibodies binding to MCF7 using flow cytometry.

As shown in FIG. 5, the chimeric antibody (cGBH) binds well to MCF7 cells. However, humanization significantly reduces this binding (see GBH(HH)). After first round back mutation, GBH(B1) recovered most binding activity of the antibody. Further mutations, GBH(Re1Re2) and GBH (re2Re2), significantly improved the binding affinities. The sequences of the light-chain and heavy-chain variable domains for these mutants are shown in FIGS. 8A and 8B.

4) CDR Affinity Optimization and Alanine Scanning of Critical Amino Acid Residues In addition to the above-described back mutations in the framework regions, antibody affinities may be further improved by optimizing CDR sequences. Based on computer modeling and computational docking of Globo H antigen with GBH(Re2Re2) antibody, selective CDR mutant clones were generated by site-directed mutagenesis. The binding affinities of the mutated clones may be analyzed with any suitable methods, such as by ELISA, Biacore, or ForteBio.

Table 1 shows an example of alanine-scanning results, using GBH(Re2Re2) as the starting antibody. These results show that alanine substitutions at 4 sites (I33 in CDRH1, R50 in CDRH2, E96 in CDRH3, and W27 in CDRL1) resulted in marked reduction in the antibody affinity, indicating that these 4 residues are critical for antibody bindings. On the other hand, alanine substitutions at other sites (e.g., N58 in CDRH2, N28 in CDRL1, D93 in CDRL1, and I94 in CDRL3) do not significantly impact the antibody binding, indicating that these residues are not critical for antigen-antibody interactions.

TABLE 1

Results from Alanine Scanning of CDR residues

| Clone Name | CDR | Mutant Site | Sub. AA | KD (M)* |
|---|---|---|---|---|
| Re2Re2 | | | | 3.37E−09 |
| VHB1 | H1 | I33 | A | *** |
| VHB2 | H2 | R50 | A | *** |
| VHB3 | H2 | N58 | A | 5.24E−09 |
| VHB4 | H3 | E96 | A | *** |
| VLB1 | L1 | W27 | A | *** |
| VLB2 | L1 | N28 | A | 3.46E−09 |
| VLB3 | L3 | D93 | A | 2.32E−10 |
| VLB4 | L3 | I94 | A | 1.78E−08 |

* ELISA measurements

Figure 6:
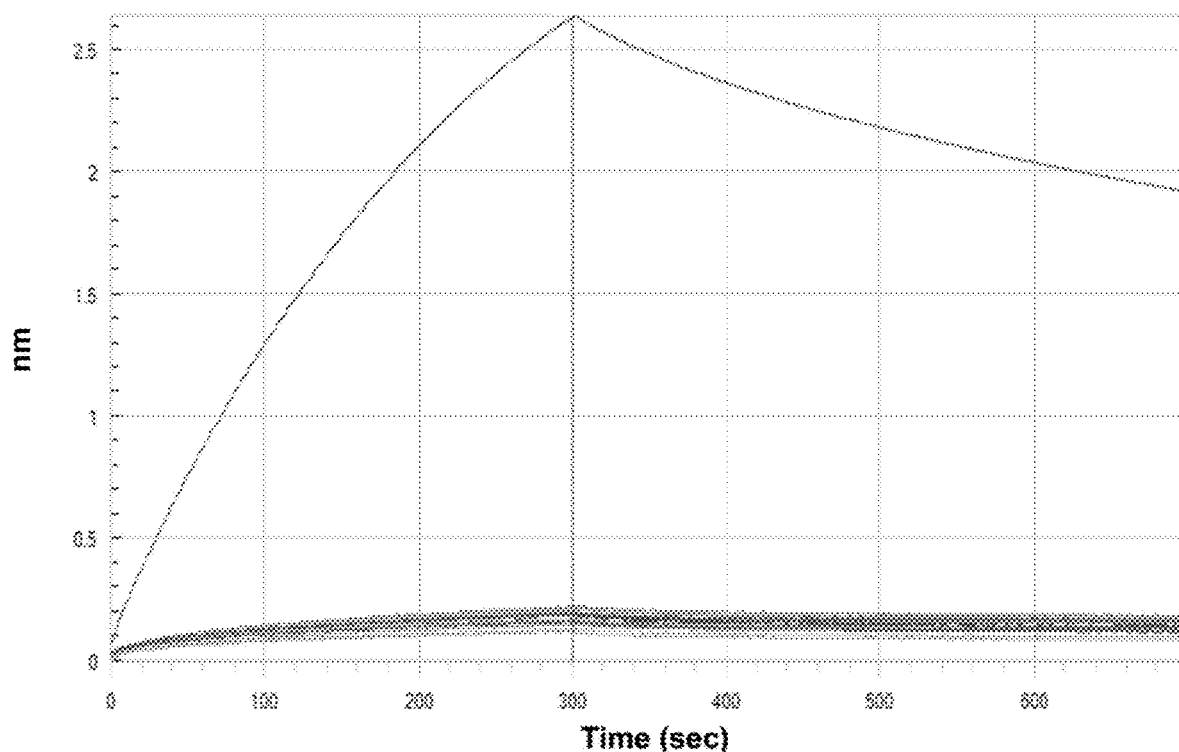
FIG. 6 shows results of various amino acid replacement of R50 in the heavy-chain variable domain ($V_H$). The results show that replacement of this R50 with any other amino acid markedly reduces the binding affinity of the anti-Globo H antibody, indicating that this R50 is essential for antigen-antibody interactions.

The critical residues from the above alanine scanning can be further tested to corroborate the importance of these critical residues. As shown in FIG. 6, R50 in CDRH2 is a critical residue and substitutions with any other amino acids essentially abolished the binding.

Figure 7:
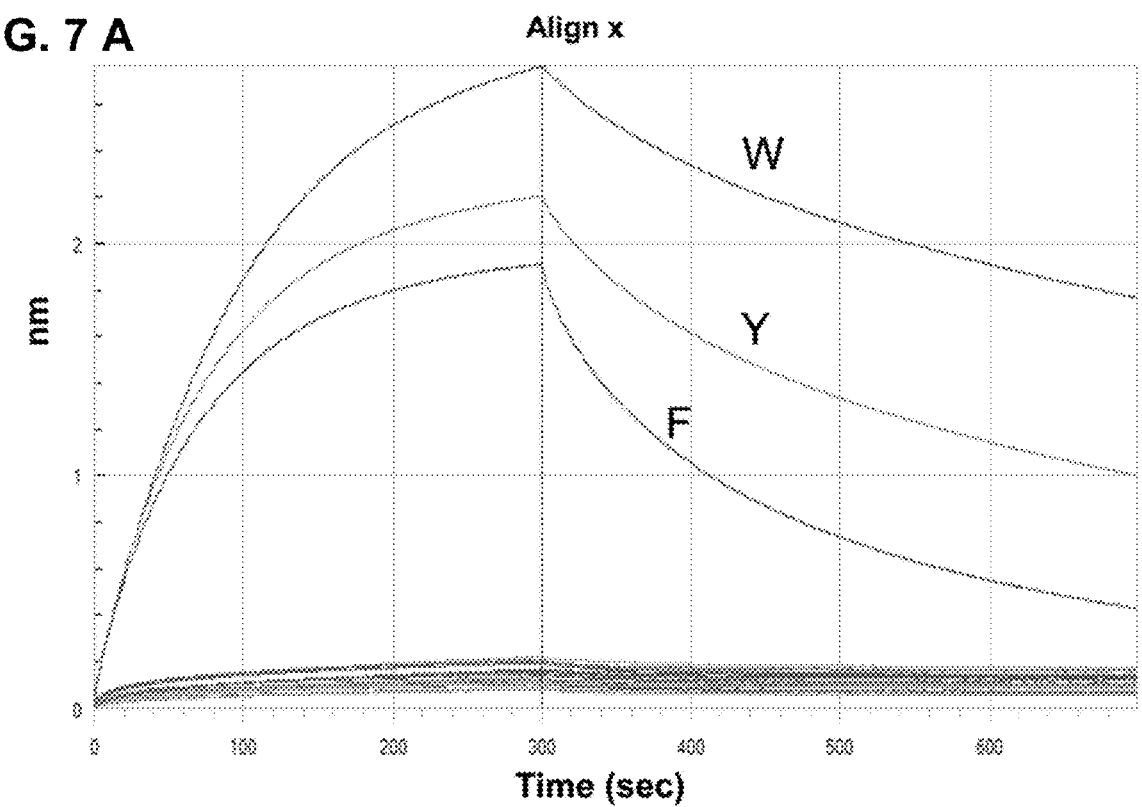
FIG. 7A shows results of various amino acid replacement of W27 in the light-chain variable domain ($V_L$). The results show that replacement of this W27 with other aromatic amino acids results in slight reduction in antibody affinities. However, replacements with non-aromatic amino acids markedly reduce the binding affinity of the anti-Globo H antibody.
FIG. 7B shows result of various amino acid replacement of N55 in the heavy-chain variable domain (VH). The results show that replacement of this N55 with many other amino acids are tolerated at this site. Among the various amino acid replacements, glutamine (Q) replacement actually produced a tighter antibody.
Figure 7:
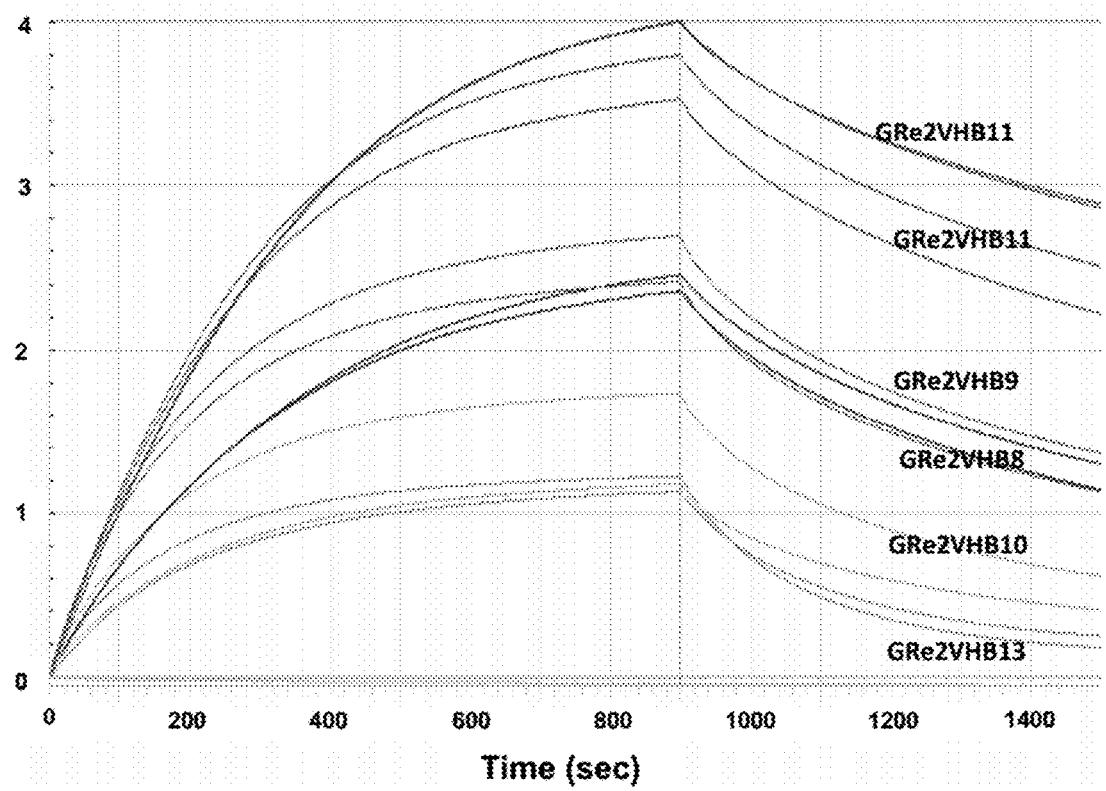

On the other hand, some apparently critical residues by alanine scanning may tolerate similar amino acids. For example, as shown in FIG. 7A, while W27 in LCDR1 (see FIG. 9B) is important for binding, replacement with other aromatic amino acid residues (Y and F) are well tolerated, though other amino acid substitutions at this site essentially abolished the antibody binding. These results indicate that as long as the amino acid residue with an aromatic side chain is at this location, the antibody binding activity is substantially preserved.

On the other hand, amino acids that are not critical from alanine scanning results may be further optimized. For example, residue 58 (shown as X' in HCDR2 in GBH (C) in FIG. 9A) is not critical and many amino acids are well tolerated at this location (FIG. 7B). Among them, glutamine (Q) gives the best binding activity. Similarly, residue 32, shown as Z in LCDR1 (FIG. 9B), can tolerate several amino acids with similar polarities. In an exemplary antibody GBH (B13) this Z is threonine (FIG. 9B).

Other residues in CDRs were also investigated to see whether replacements with other amino acids (i.e., other than alanine) would result in improved bindings. As shown in TABLE 2, only replacement of N58 with Q (clone name: VHB11) resulted in slight improvement of binding. All other amino acid replacements of critical residues resulted in loss or reduced binding.

TABLE 2

| Clone Name | CDR | Mutant Site | Sub AA | KD value (ForteBIO) | Binding |
|---|---|---|---|---|---|
| Re2Re2 | | | | 1.13E−08 | |
| VHB5 | H1 | I33 | Q | | x |
| VHB6 | H2 | Y52 | N | | x |
| VHB7 | H2 | Y52 | R | | x |
| VHB8 | H2 | T54 | Q | | Weak |
| VHB9 | H2 | V56 | N | | Weak |
| VHB10 | H2 | V56 | Q | | Weak |
| VHB11 | H2 | N58 | Q | 1.06E−08 | Strong |
| VHB12 | H2 | N58 | R | | x |
| VHB13 | H3 | T97 | Q | | Weak |
| VHB14 | H4 | T97 | R | | x |

FIG. 8A shows the sequence alignment for the framework regions of the heavy-chain variable domain of mouse clone (M) (SEQ ID NO:10), humanized clone (H) (SEQ ID NO:11), back mutated clone (B1) (SEQ ID NO:12), repeat back mutated clone (Re2) (SEQ ID NO:13), and VHB11 clone (B11) (SEQ ID NO:14). FIG. 8B shows the sequence alignment for the framework regions of the light-chain variable domain of mouse clone (M) (SEQ ID NO:15), humanized clone (H) (SEQ ID NO:16), back mutated clone (B1) (SEQ ID NO:17), repeat back mutated clone (Re2) (SEQ ID NO:18), and VHB11 clone (B11) (SEQ ID NO:19).

In CDRL1, residue-32 is not critical for binding. Several residues, C, S, G, and T, are acceptable. As an example, Clone B13 having T at this location is shown in FIG. 9B.

FIG. 9A shows the sequences for the heavy-chain variable domains for a consensus clone GBH (C) (SEQ ID NO:20) and an exemplary clone GBH (B13) (SEQ ID NO:21). FIG. 9B shows the sequences for the light-chain variable domains for a consensus clone GBH (C) (SEQ ID NO:22) and an exemplary clone GBH (B13) (SEQ ID NO:23).

Affinity Determination Assay—ForteBio

To assess anti-Globo H antibody affinities, Globo H-amine was immobilized on the amine-reactive biosensor according to the manufacturer's instructions. All the measurements were performed at 30° C. using ForteBio Octet Red96. Affinity binding curve fit was performed using predefined model (1:1 binding) provided by Octet Data Analysis software.

Table 3 shows results from ForteBio assays of some examples.

TABLE 3

| | Analyte Biotin-GloboH | | |
|---|---|---|---|
| Antibodies | Ka | Kd | KD |
| Re2Re2-131209 | 4.86E+4 | 2.13E−3 | 4.37E−8 |
| Re2VLB3-131209 | 5.56E+4 | 1.79E−3 | 3.22E−8 |
| Re2VLB4-131209 | 2.16E+1 | 1.15E−3 | 5.34E−5 |
| Re2VHB4-131209 | 8.31E+3 | 1.95E−2 | 2.34E−6 |

Fluorescence Imaging

Antibodies of the invention may be used to visualize cells that express Globo H, for example in diagnosis of cancers expressing Globo H. As an example, to visualize anti-Globo H antibody bound to Globo H expressed on the cell surfaces (e.g., MCF7 cells), MCF7 cells were cultured on glass slides (NUNC) and then fixed with 4% paraformaldehyde. After PBS washes, the cells were stained with anti-Globo H antibody and followed by goat anti-human FITC antibody (1:1000; Thermo Scientific). Cells without primary antibody were included as controls. Mounted slides were examined by FITC fluorescence and bright-field images by fluorescence microscopy (Olympus).

Figure 10:
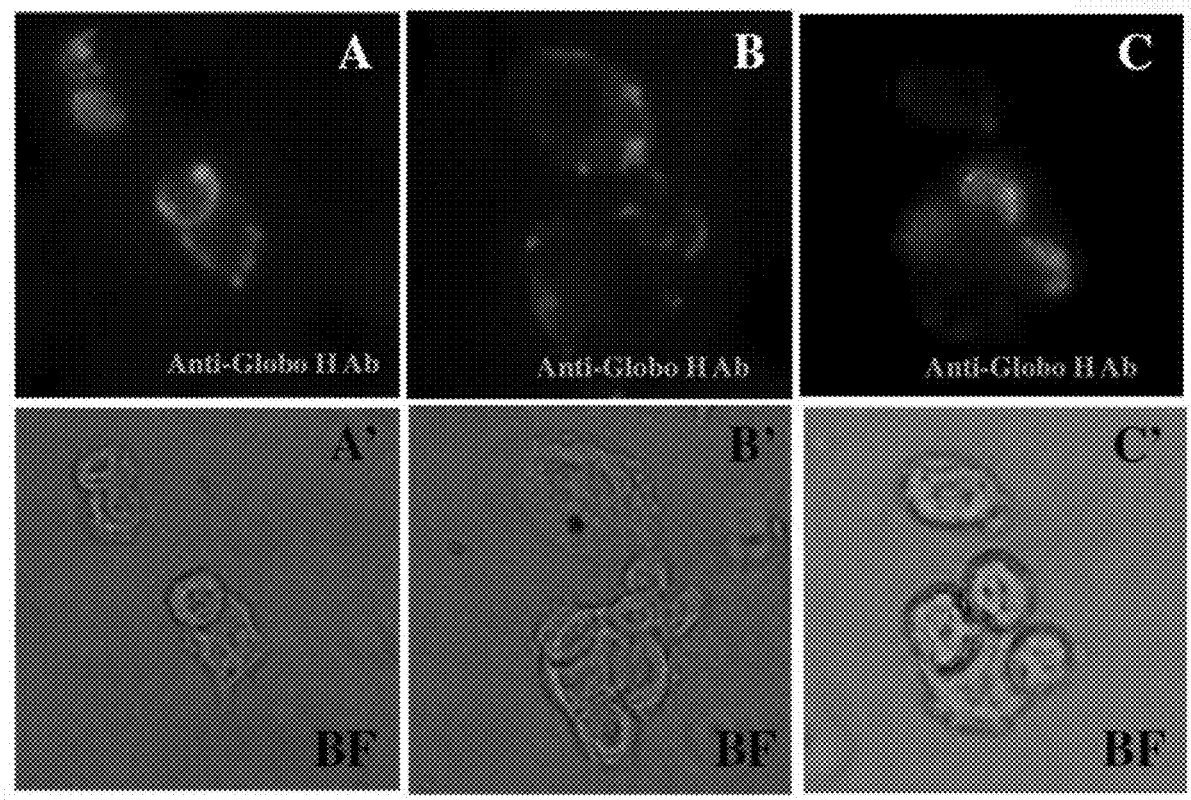
FIG. 10 shows recognition of breast cancer cells expressing Glob H by anti-Globo H antibodies. Panels A-C show immunofluorescence images of antibody recognitions of the MCF7 cells. Panels A'-C' show the corresponding images of cells visualized with an optical microscope.

FIG. 10 shows the results of immunostaining of MCF7 cells with an anti-Globo H antibody. Panels A-C show fluorescence imaging of MCF7 cells with anti-Globo H Ab, and panels A'-C' show black field (BF) imaging of the same cells. These results show that antibodies of the invention can indeed bind Globo-H on cell surfaces.

Affinity Determination Assay—Biacore™

Antibody affinity may be assessed with ELISA or BiaCore™. For BiaCore™ assays, Globo H-amine was immobilized on a Biacore™ CM5 chip (Biacore, Uppsala, Sweden) using standard amine chemistry according to the manufacturer's instructions. Independent serial dilutions of the anti-Globo H antibodies were prepared on a microplate. Each sample was injected for 2.5 min, for example, at a flow rate of 50 µL/min over two flow cells: one control cell and the other with immobilized Globo H. The binding kinetics was measured at the end of injection. After each sample, the chip was regenerated by injection of 10 mM glycine pH 2.5/1.5 (v/v=1) at a flow rate of 30 µL/min for 45 seconds. All experiments were carried out in HBS-EP buffer (Biacore™) at a constant temperature of 25.0° C. using Biacore T100 instruments. Affinity binding curve fit was performed using predefined model (1:1 binding) provided by Biacore T100 evaluation software 2.0.

Fluorescence-Activated Cell Sorting (FACS)

Anti-Globo H antibodies may be used to detect cells that express Globo H on the cell surfaces or to sort cells expression Globo H, for example using FACS. Globo H expressing cells, MCF7 or HCC1428, were harvested and re-suspended in 5% PBS/FBS buffer. Cells ($1\times10^5$) were incubated with anti-Globo H antibody (10 µg/ml) or Herceptin (10 µg/ml, negative control) at 4° C. for 1 hr, and then stained with goat anti-human IgG FITC conjugate (1/1000) at 4° C. for 1 hr. For each assay, two additional controls were prepared; one without primary antibody and the other one with absence of any antibody. All treated samples were analyzed with FACSVerse (Becton Dickinson) and the results were processed by FAC Suite software (Becton Dickinson).

Figure 11:
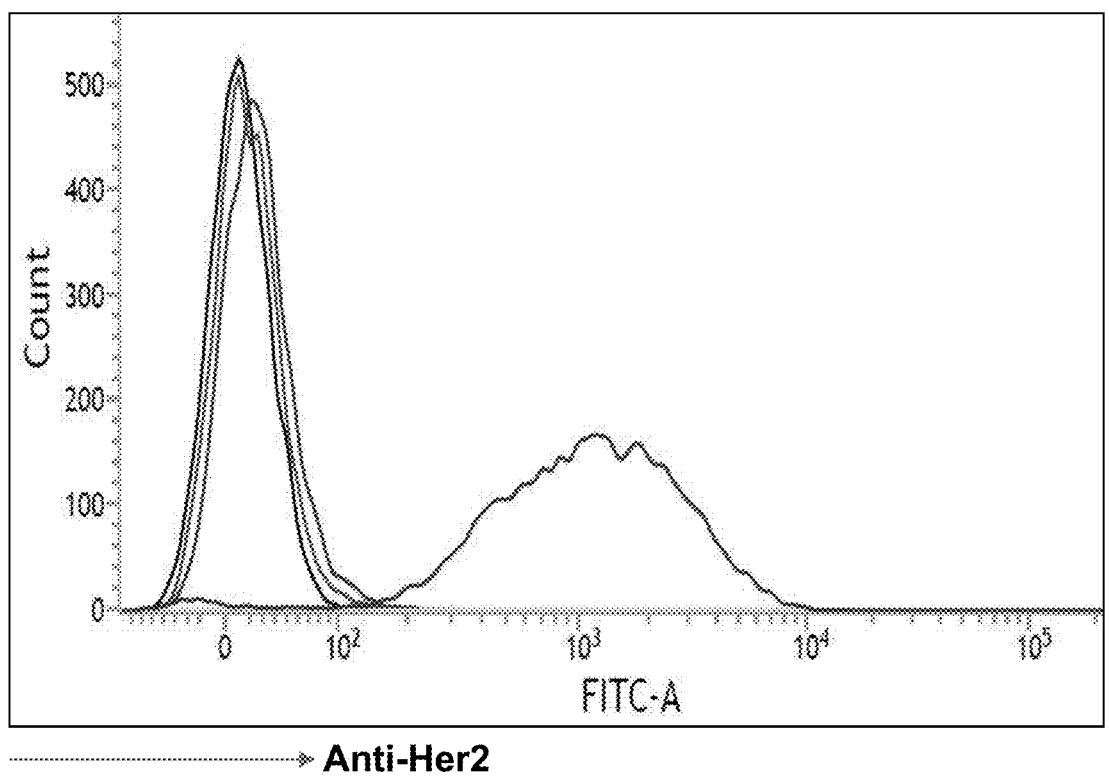
FIGS. 11A-11J show FACS results, indicating expression of Glob H on various cancer cells as detected by anti-Globo H antibodies.
Figure 11:
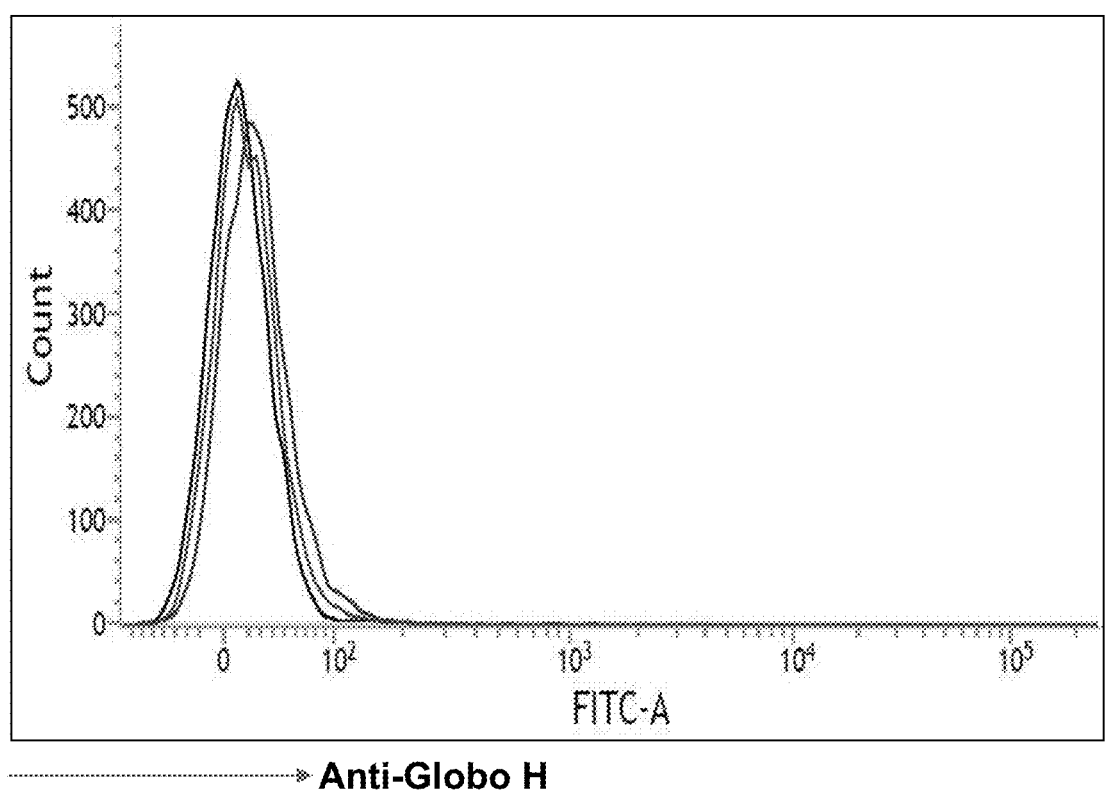
Figure 11:
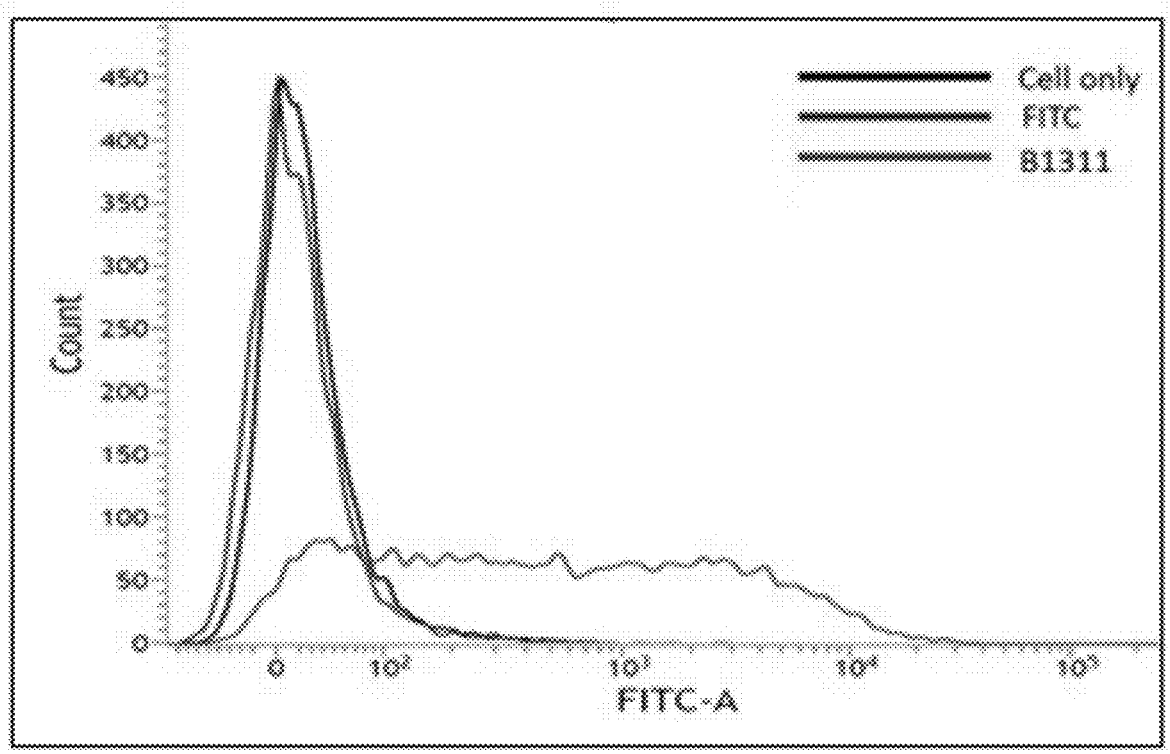
Figure 11:
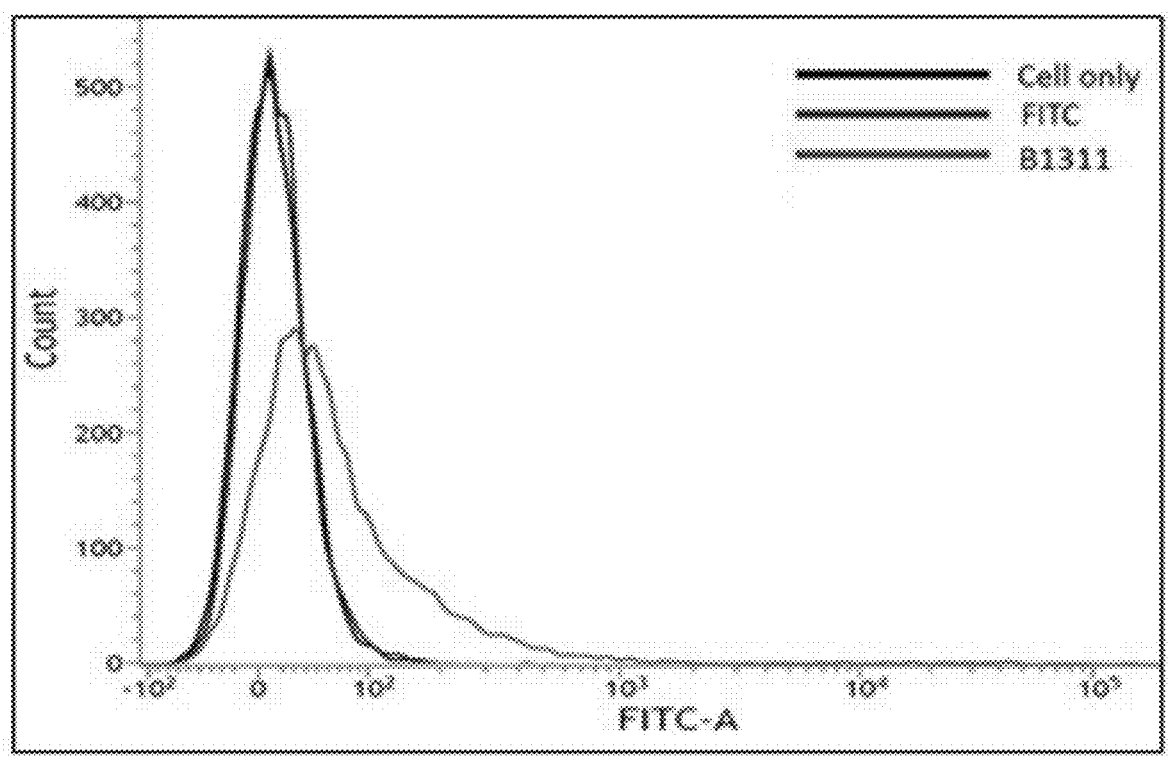
Figure 12:
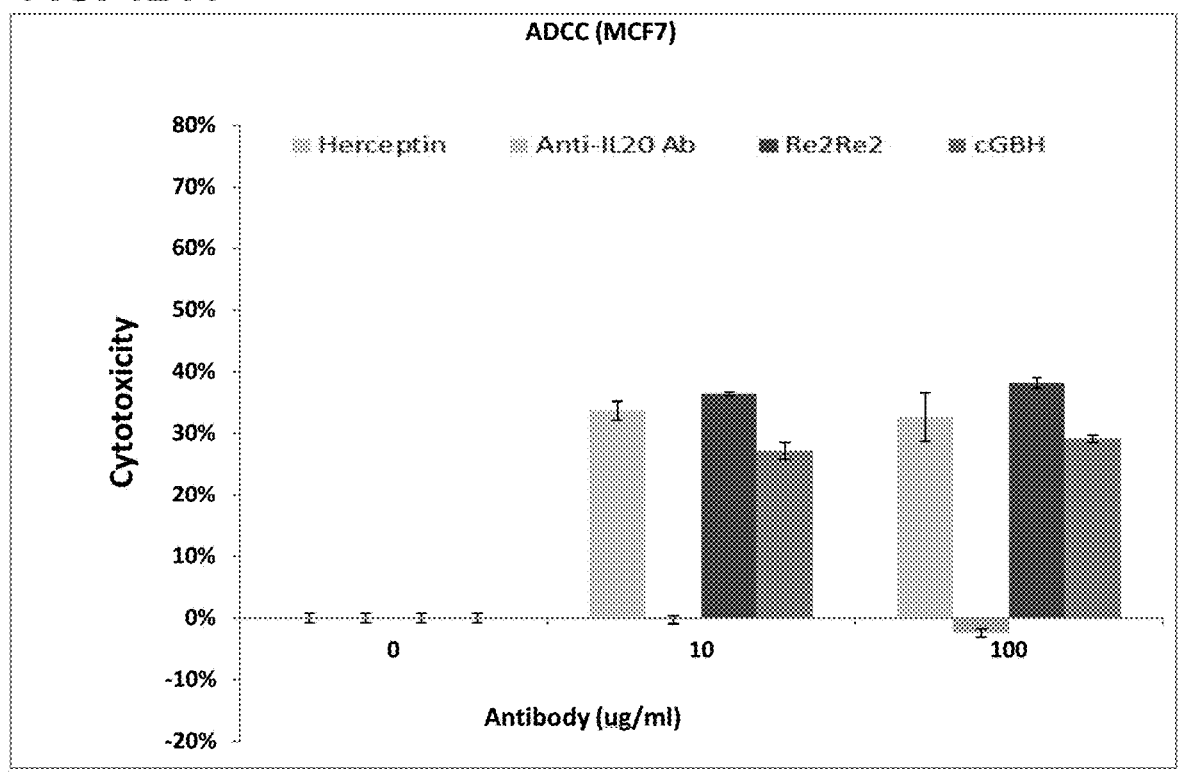
FIGS. 12A-12F show results of antibody-dependent cell cytotoxicity (ADCC) mediated by anti-Globo H antibodies.
Figure 12:
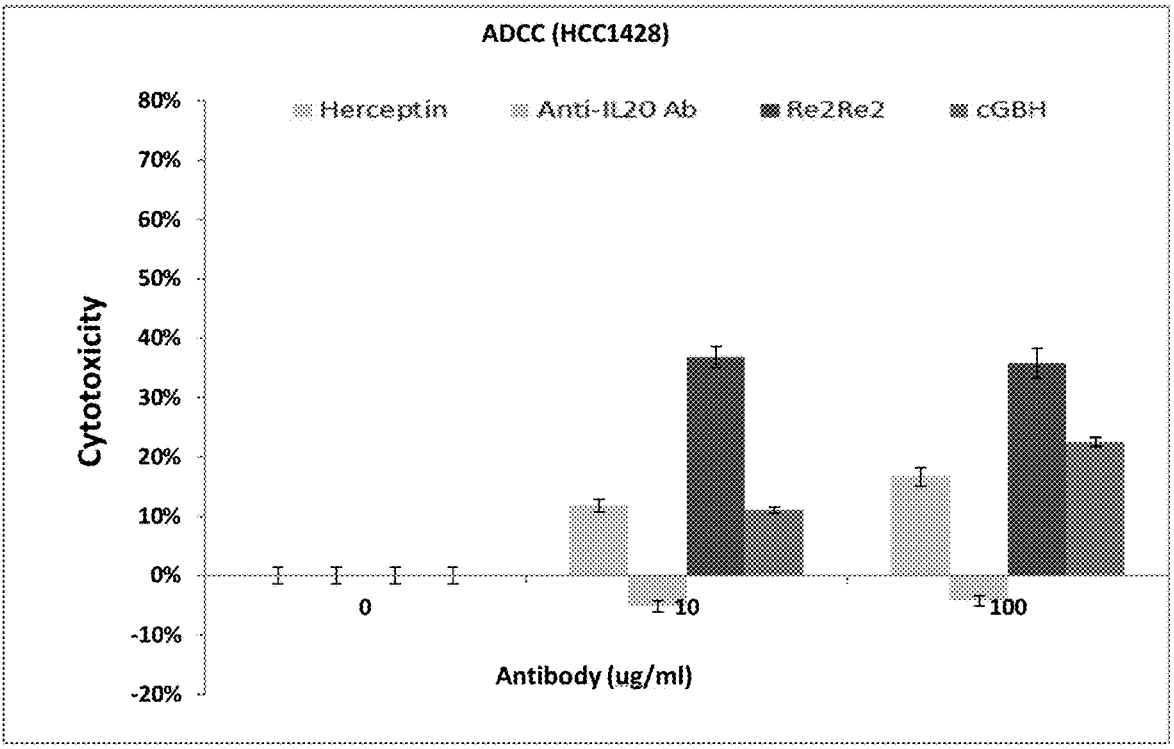
Figure 12:
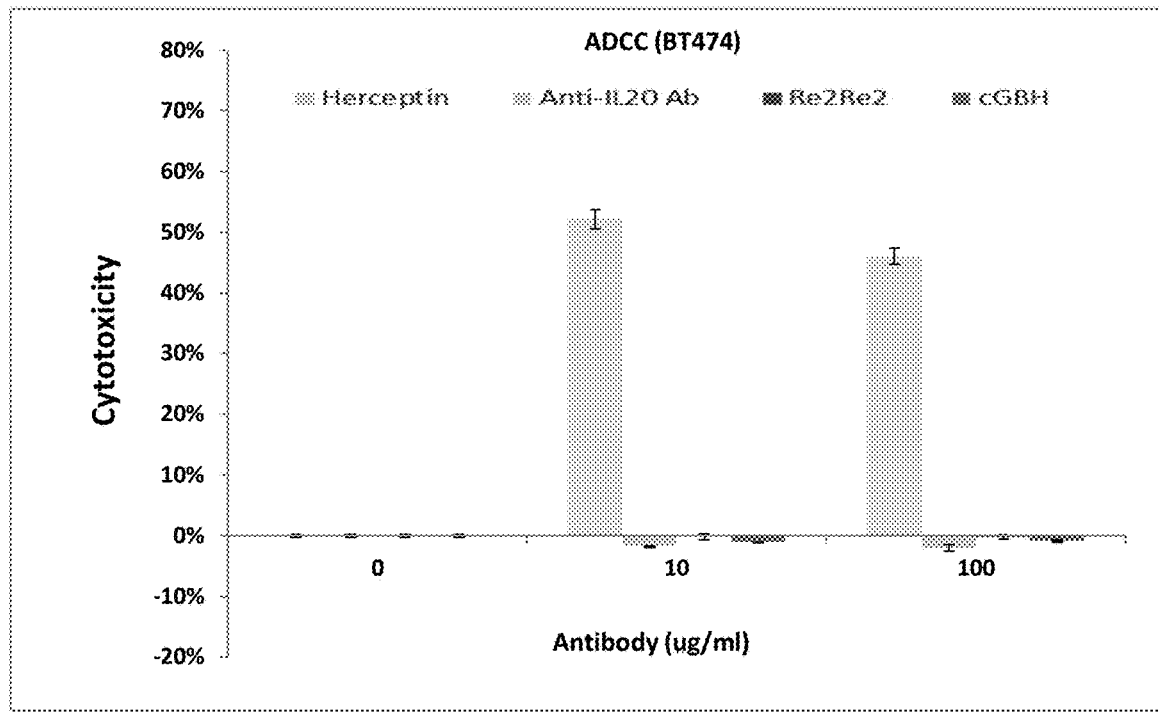
Figure 12:
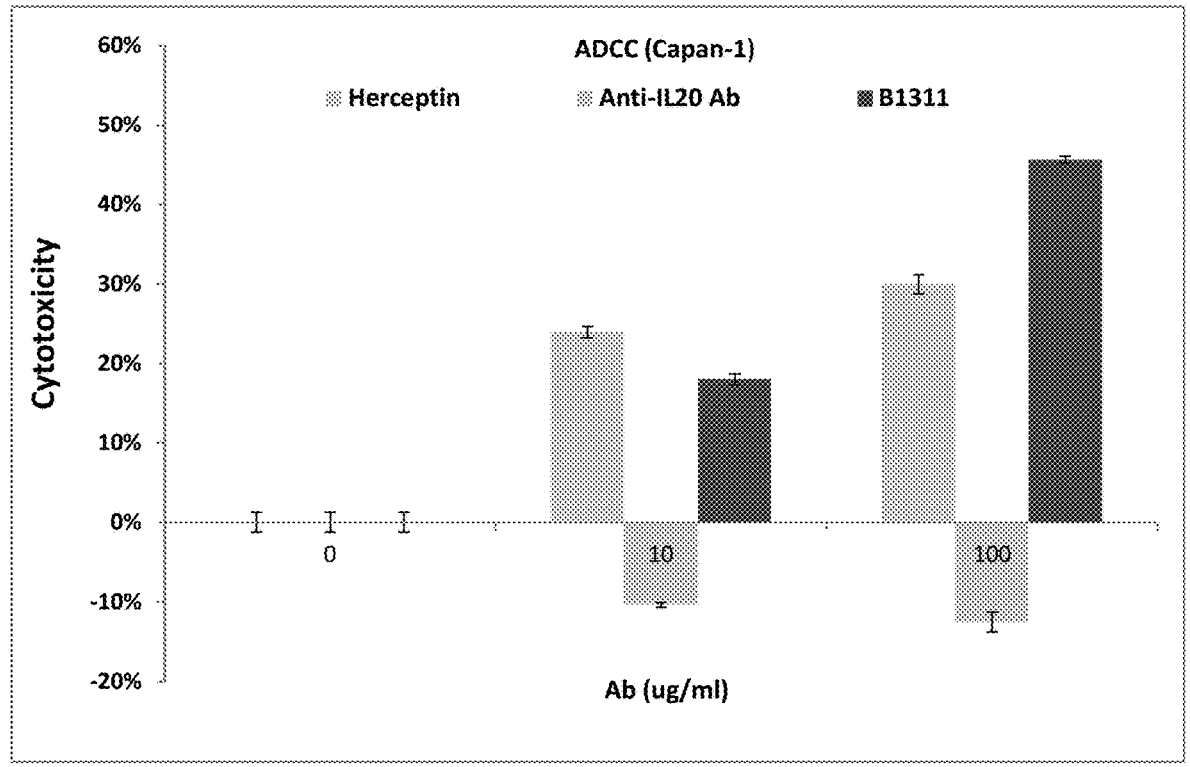
Figure 12:
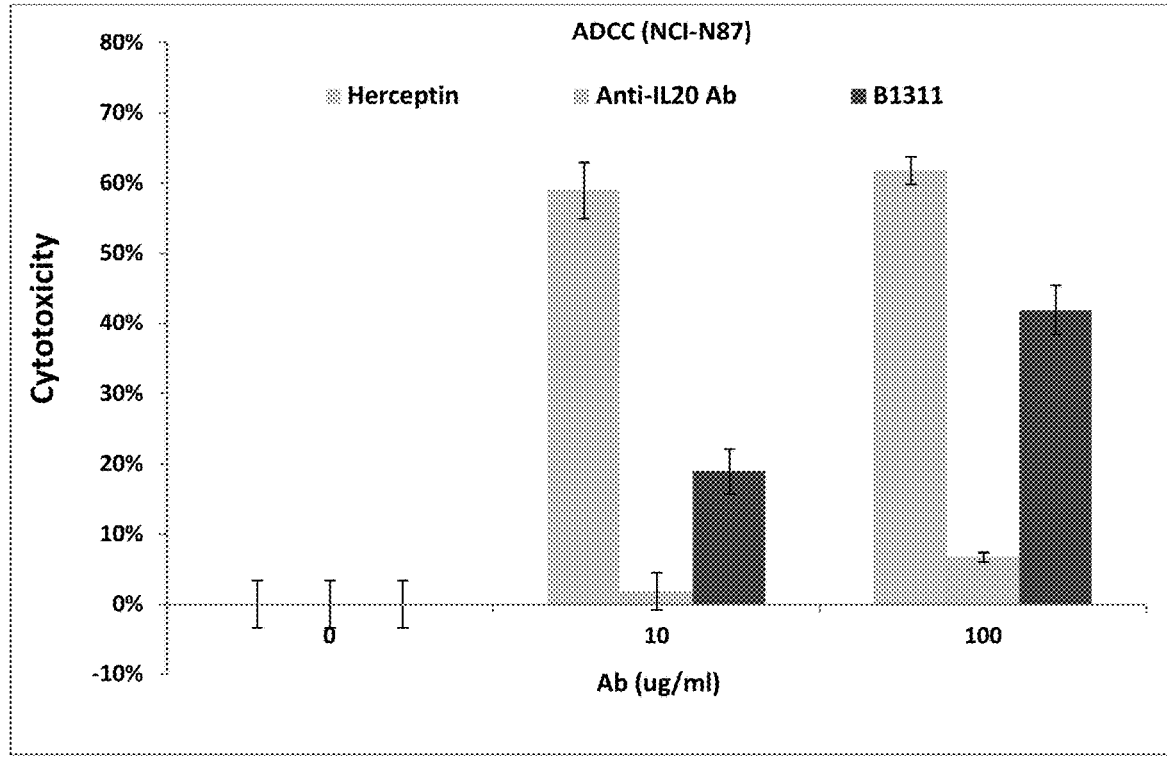
Figure 12:
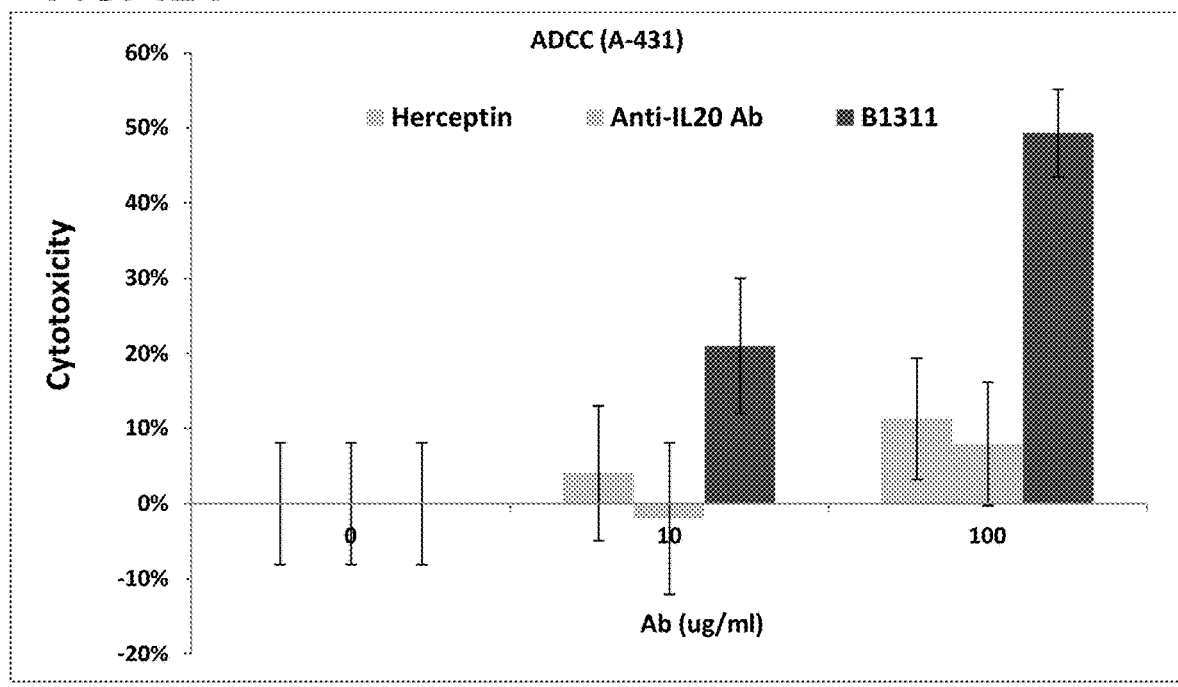

Based on the FACS, various cancer cells may be assessed to see whether they express Globo H. FIGS. 11A-11J show results of Globo H detections from various cell lines using anti-Globo H antibodies and FACS. FIG. 11A shows that MCF7 breast cancer cells express Her2 antigen, and FIG. 11B shows that MCF7 breast cancer cells express Globo H antigen. FIG. 11C shows that HCC1428 hepatoma cells express Her2 antigen, and FIG. 11D shows that HCC1428 hepatoma cells express Globo H antigen. FIG. 11E shows that BT474 breast cancer cells express Her2 antigen, but not Globo H (FIG. 11F). Similarly, FIG. 11G shows that Capan-1 pancreatic cancer cells express Globo H. FIG. 11H shows that A-431 squamous carcinoma cells express Globo H. FIG. 11I shows that NCI-N87 gastric cancer cells express Globo H. FIG. 11J shows that HT-29 colorectal cancer cells express low level of Globo H. These results demonstrate the utility of anti-Globo H antibodies in the diagnosis of various cancers.

Antibody-Dependent Cell-Mediated Cytotoxicity (ADCC)

Antibody-dependent cell-mediated cytotoxicity (ADCC) plays an important role in antibody-based cancer therapy. The humanized anti-Globo H antibodies of the invention are promising therapeutics for treating cancers that express Globo H. To assess the ADCC activities of the anti-Globo H antibodies, purified human NK cells were incubated with antibody-treated human breast carcinoma cells (e.g., HCC1428, MCF7, Capan-1, NCI-N87, A431, or BT474 cells) at 5:1 E/T ratio for 3 hrs. An anti-IL20 antibody was used as a negative control and Herceptin (Roche) was used as a positive control for the ADCC assays. Percentages of cell death were measured using TDA releases with the DELFIA EuTDA Cytotoxicity Reagents Kit (PerkinElmer). The fluorescence was measured in the time-resolved fluorometer (CLARIO, BGM).

FIGS. 12A-12F show that anti-Globo H antibodies are capable of inducing ADCC in various cancer cells, including MCF7 (FIG. 12A), HCC1428 (FIG. 12B), Capan-1 (FIG. 12D), NCI-N87 (FIG. 12E), and A431 (FIG. 12F) cancer cells. However, the anti-Globo H antibody was not able to induce ADCC in BT474 cells, consistent with the observation that BT474 cell (FIG. 12C) do not express Glob H on surfaces. These results support that the anti-Globo H antibody induced ADCC is dependent on the expression of Globo H on cell surfaces and confirms that anti-Glob H antibodies would be effective in inducing killing of cancer cells that express Globo H.

Complement Dependent Cytotoxicity (CDC)

Similar to ADCC, complement-dependent cytotoxicity (CDC) plays an important role in antibody-based cancer therapy. To assess the abilities of anti-Globo H antibodies of the invention in inducing CDC, the following experiments were conducted. In these tests, 40% of Normal Human Serum (NETS) (v:v) were added to the antibody-treated human cancer cells, including HCC1428, MCF7, BT474, Capan-1, or NCI-N87 cells, for 3 hrs. Both the anti-IL20 antibody and Herceptin was used as negative control for CDC assay. Percentage of cell death was measured using TDA release with DELFIA EuTDA Cytotoxicity Reagents Kit (PerkinElmer). The fluorescence was measured in the time-resolved fluorometer (CLARIO, BGM).

Figure 13:
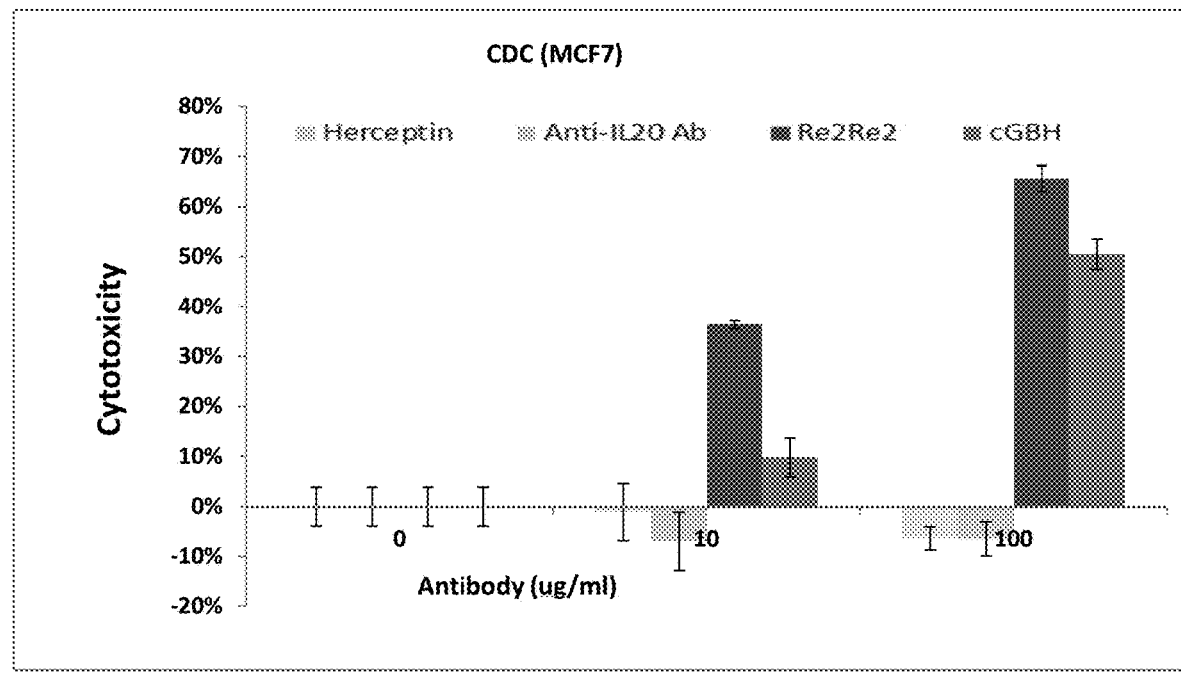
FIGS. 13A-13E show results of complement-dependent cytotoxicity (CDC) mediated by anti-Globo H antibodies.
Figure 13:
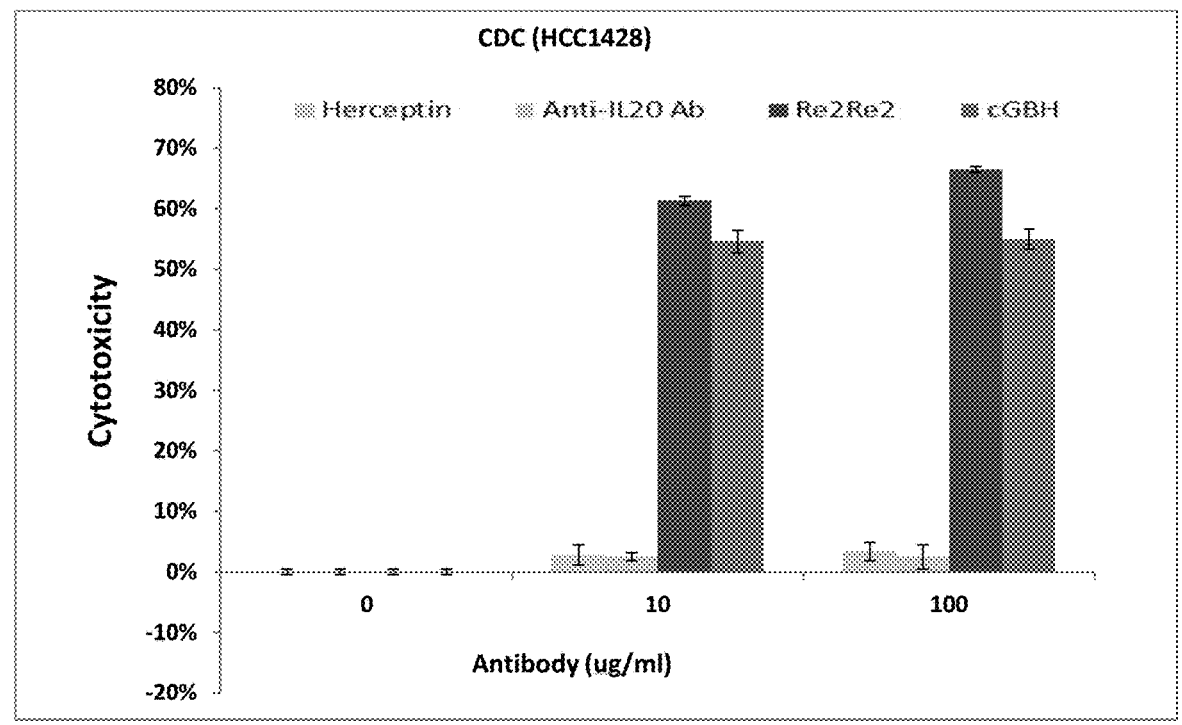
Figure 13:
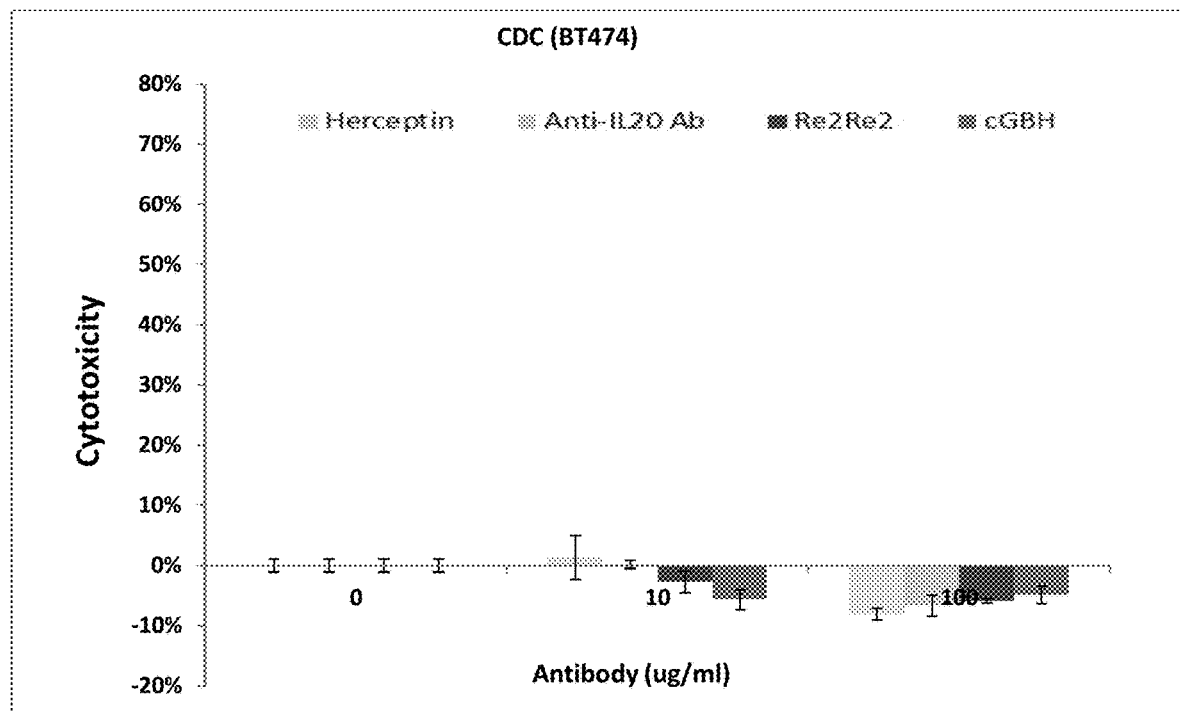
Figure 13:
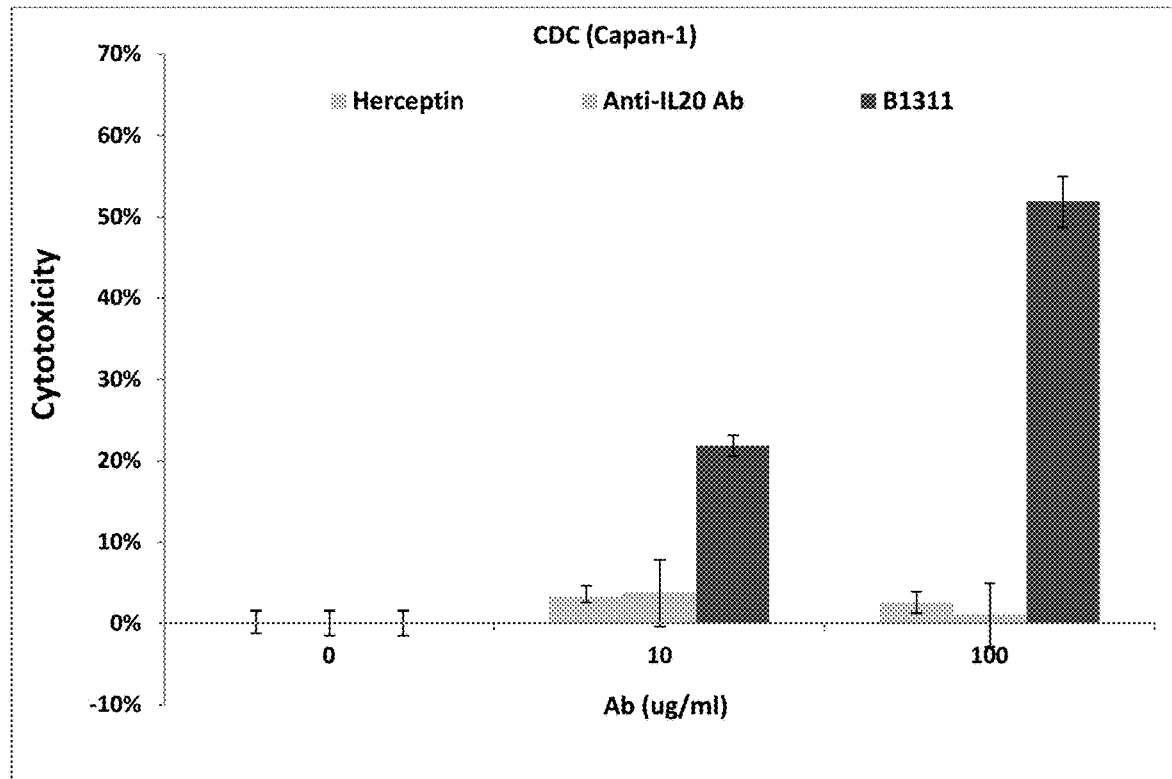
Figure 13:
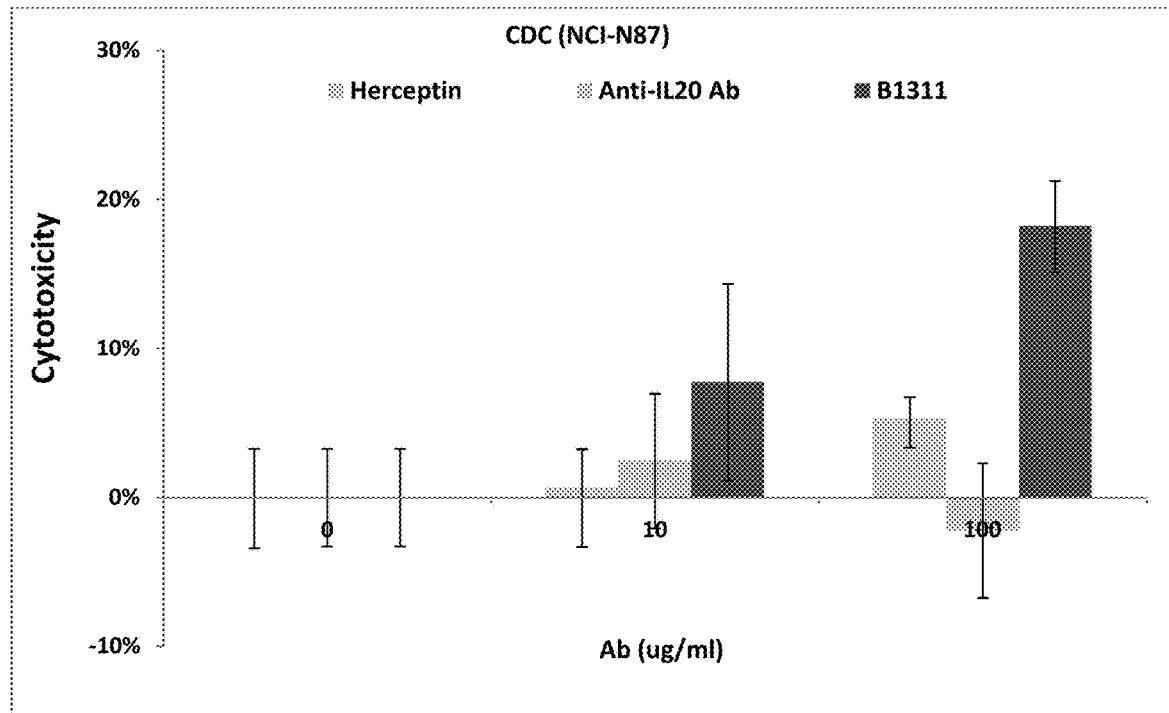

FIGS. 13A-13E show that anti-Globo H antibodies could induce CDC in MCF7 cells (FIG. 13A), HCC1428 cells (FIG. 13B), Capan-1 cells (FIG. 13D), and NCI-N87 (FIG. 13E) cells. However, the anti-Globo H antibody could not induce CDC in the BT474 cells (FIG. 13C). These results are consistent with the fact that MCF7, Capan-1, NCI-N87, and HCC1428 cells express Globo H on their surfaces, while BT4747 cells do not. These results confirm that the anti-Globo H antibodies can induce CDC and that CDC induced by anti-Globo H antibodies depends on the expression of Globo H on cell surfaces.

Globo H Competition Assay

To confirm that the anti-Globo H antibody induced cytotoxicity is Globo H dependent, one can perform Globo H competition. 1 µM of anti-Globo H antibody were pre-incubated with various concentrations of either synthetic Globo H or Lewis-b tetrasaccharide (Sigma) at 37° C. for 1 hr. Lewis-b tetrasaccharide was used as negative control. 40% of NHS (v:v) were added to the anti-Globo H antibody-Glycan mixture and then incubated with human breast carcinoma cell line MCF7 for 3 hrs. Percentage of cell death was measured using TDA release with DELFIA EuTDA Cytotoxicity Reagents Kit (PerkinElmer). The fluorescence was measured in the time-resolved fluorometer (CLARIO, BGM).

Figure 14:
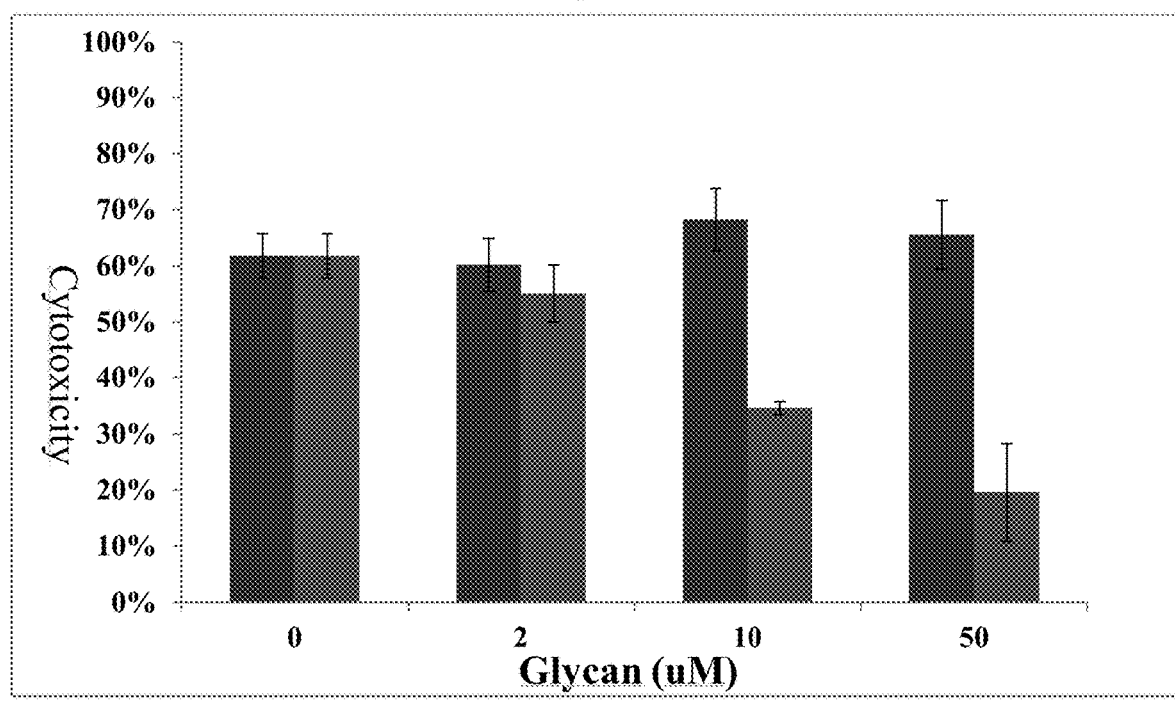
FIG. 14 shows results of inhibition of anti-Globo H antibody-mediated cell cytotoxicity by synthetic glycans. The results show that Globo H can compete and inhibit anti-Globo H antibody mediated cell cytotoxicity in a dose-dependent manner, while Lewis-b tetrasaccharide cannot. This specific competition indicates that anti-Globo H mediated cell cytotoxicity is by binding to Globo H expressed on the cell surface.

FIG. 14 shows that anti-Globo H induced cytotoxicity can be competed with Globo H (Fucose-Galactose-N—Ac-Galactosamine-Galactose-Galactose-Glucose) in a dose-dependent manner, but not with Lewis-b tetrasaccharide (Fucose-Galactose-N—Ac-Glucosamine-Fucose). These results further confirm that the cytotoxicity induced by anti-Globo H antibodies are Globo H dependent.

Xenograft Animal Model

The fact that anti-Globo H can induce ADCC and CDC of Globo H expressing cells indicate that these antibodies are useful in preventing and/or treating cancers that express Globo H on their surfaces.

To assess the abilities of anti-Globo H antibodies in preventing and/or treating cancers, groups of 5 female (NOD/SCID) mice weighing 20-24 g (6-7 weeks old) are used. Viable human breast carcinoma HCC1428 cells (provided by Sponsor, $1\times10^7$ in 0.2 ml in matrigel) are injected subcutaneously into the dorsal side of nude mice. Estol-Depot (100 µg/mouse) is injected subcutaneously twice weekly starting one week before cell implantation as a supplement for 7 weeks. Test reagents (anti-Globo H antibody, taxol, or vehicle) are administered intravenously starting 2 hrs (prophylatic model) or 7 days (treatment model) after cell implantation. Body weight and tumor size are recorded twice weekly for up to 60 days. Tumor weight ($mm^3$) is estimated according to the formula for a prolate ellipsoid: length (mm)×[width (mm)]$^2$×0.5. Tumor growth in test compound treated animals is calculated as T/C (Treatment/Control)×100%; a value of T/C 42% is considered significant in demonstrating antitumor activity.

Figure 15:
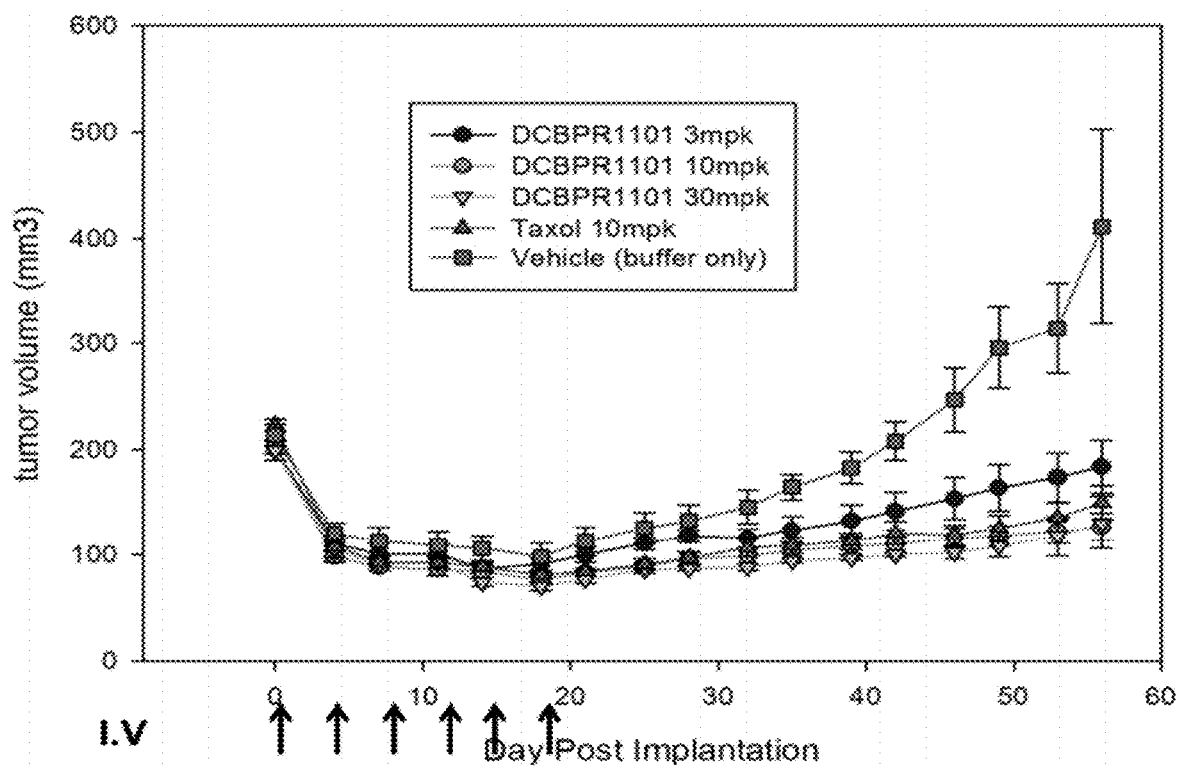
FIG. 15 shows that humanized anti-Globo H antibody can inhibit tumor growth in a dose-dependent manner in a prophetic model.

FIG. 15 shows that, in a prophylactic model, the anti-Globo H antibody was able to prevent tumor growth in a dose-dependent manner. At a dose of 10 mg/Kg (mpk), the antibody is as effective as taxol, and at 30 mpk, the antibody was more effective than taxol in preventing cancer growth.

Figure 16:
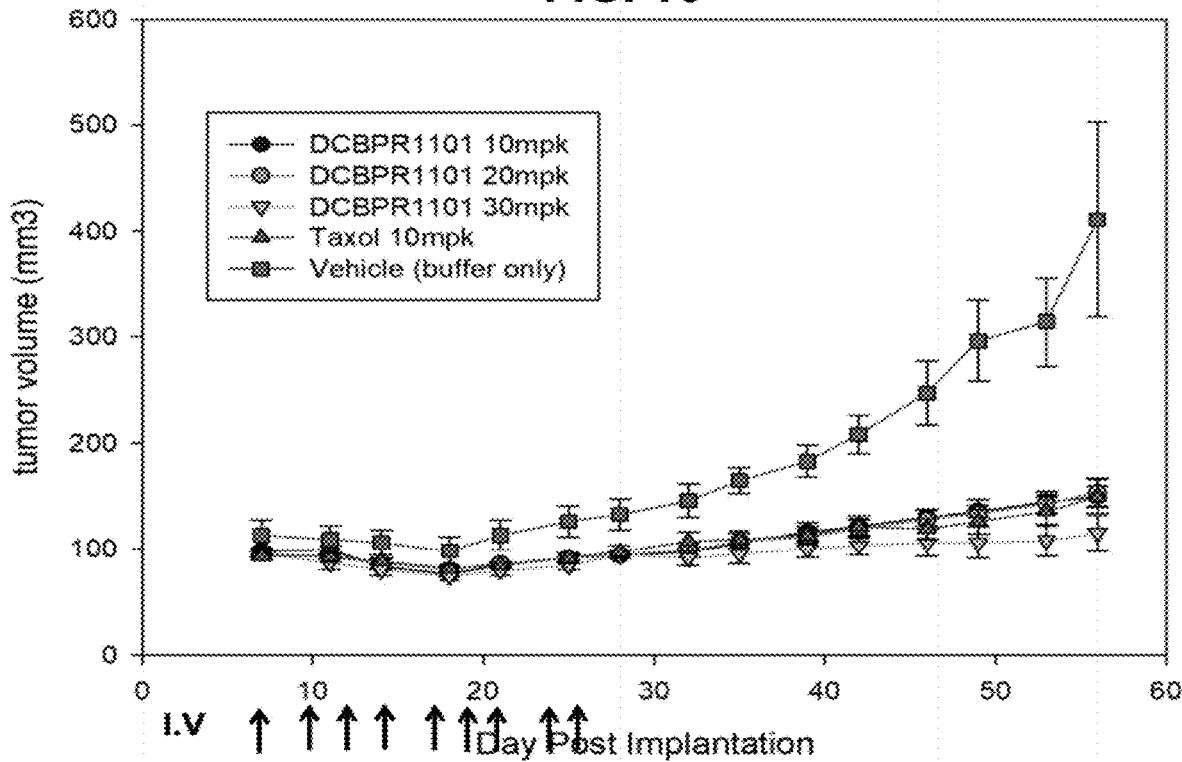
FIG. 16 shows that humanized anti-Globo H antibody can inhibit tumor growth in a dose-dependent manner in a therapeutic model.

FIG. 16 shows that, in a treatment model, the anti-Globo H antibody was able to suppress tumor growth in a dose-dependent manner. At a dose of 10 mg/Kg (mpk), the antibody is as effective as taxol, and at 20 mpk and 30 mpk, the antibody was more effective than taxol in preventing cancer growth.

Results from these in vivo models indicate that humanized anti-Globo H antibodies can be used in the prevention and treatment of cancers expressing Globo H, e.g., various epithelial cancers, including breast, colon, ovarian, pancreatic, lung, liver, and prostate cancers.

What is claimed is:

1. A humanized anti-Globo H antibody, or an antigen-binding fragment thereof, comprising a heavy-chain variable domain having three complementarity-determining regions consisting of HCDR1, HCDR2, and HCDR3 and a light-chain variable domain having three complementarity-determining regions consisting of LCDR1, LCDR2, and LCDR3, wherein the sequence of HCDR1 is GYISSDQILN (SEQ ID NO:4), the sequence of HCDR2 is RIYPVTGVTXYNHK-FVG (SEQ ID NO:5, wherein X is any amino acid), and the sequence of HCDR3 is GETFDS (SEQ ID NO:6), wherein the sequence of LCDR1 is KSNQNLLX'SGNRRYZLV (SEQ ID NO:7, wherein X' is F, Y, or W, and Z is C, G, S or T), the sequence of LCDR2 is WASDRSF (SEQ ID NO:8), and the sequence of LCDR3 is QQHLDIPYT (SEQ ID NO:9).

2. The humanized anti-Globo H antibody, or the antigen-binding fragment thereof, according to claim 1, wherein the X in SEQ ID NO:5 is asparagine or glutamine.

3. The humanized anti-Globo H antibody, or the antigen-binding fragment thereof, according to claim 1 or 2, wherein the X' in SEQ ID NO:7 is tryptophan.

4. The humanized anti-Globo H antibody, or the antigen-binding fragment thereof, according to claim 1, 2, or 3, wherein the Z in SEQ ID NO:7 is threonine or serine.

5. The humanized anti-Globo H antibody, or the antigen-binding fragment thereof, according to claim 1, wherein the heavy-chain variable domain comprises the sequence of SEQ ID NO:20 and the light-chain variable domain comprises the sequence of SEQ ID NO:22.

6. The humanized anti-Globo H antibody, or the antigen-binding fragment thereof, according to claim 1, wherein the heavy-chain variable domain comprises the sequence of SEQ ID NO:21 and the light-chain variable domain comprises the sequence of SEQ ID NO:23.

7. A method for treating a cancer, comprising administering an effective amount of the antibody or the antigen-binding fragment thereof according to claim 1 to a subject in need thereof.

8. The method according to claim 7, wherein the X in SEQ ID NO:5 is asparagine or glutamine.

9. The method according to claim 7, wherein the X' in SEQ ID NO:7 is tryptophan.

10. The method according to claim 7, wherein the Z in SEQ ID NO:7 is threonine or serine.

11. The method according to claim 7, wherein the heavy-chain variable domain comprises the sequence of SEQ ID NO:20 and the light-chain variable domain comprises the sequence of SEQ ID NO:22.

12. The method according to claim 7, wherein the heavy-chain variable domain comprises the sequence of SEQ ID NO:21 and the light-chain variable domain comprises the sequence of SEQ ID NO:23.

13. The method according to claim 7, wherein the cancer is breast, colon, ovarian, pancreatic, lung, liver, or prostate cancer.

* * * * *